(12) United States Patent
Palazzolo et al.

(10) Patent No.: US 7,118,542 B2
(45) Date of Patent: *Oct. 10, 2006

(54) DEVICES FOR DETERMINING DEPTH OF CHEST COMPRESSIONS DURING CPR

(75) Inventors: James Adam Palazzolo, Sunnyvale, CA (US); Ronald D. Berger, Baltimore, MD (US); Henry R. Halperin, Baltimore, MD (US); Darren R. Sherman, Sunnyvale, CA (US)

(73) Assignee: Zoll Circulation, Inc., Sunnyvale, CA (US)

( * ) Notice: Subject to any disclaimer, the term of this patent is extended or adjusted under 35 U.S.C. 154(b) by 169 days.

This patent is subject to a terminal disclaimer.

(21) Appl. No.: 10/844,661

(22) Filed: May 12, 2004

(65) Prior Publication Data

US 2004/0210171 A1    Oct. 21, 2004

Related U.S. Application Data

(63) Continuation of application No. 10/280,220, filed on Oct. 25, 2002, now Pat. No. 6,827,695.

(51) Int. Cl.
*A61H 31/00* (2006.01)

(52) U.S. Cl. .......................................... 601/41; 601/44

(58) Field of Classification Search ...................... None
See application file for complete search history.

(56) References Cited

U.S. PATENT DOCUMENTS

| 4,928,674 A | * | 5/1990 | Halperin et al. ............... 601/44 |
| 4,930,517 A | | 6/1990 | Cohen |
| 4,987,783 A | | 1/1991 | D'Antonio |
| 5,262,958 A | | 11/1993 | Chui |
| 5,402,520 A | | 3/1995 | Schnitta |
| 5,496,257 A | | 3/1996 | Kelly |
| 5,513,649 A | | 5/1996 | Gevins |
| 5,831,164 A | | 11/1998 | Reddi |
| 5,876,350 A | | 3/1999 | Lo |
| 5,978,693 A | | 11/1999 | Hamilton |

(Continued)

FOREIGN PATENT DOCUMENTS

EP    1079310    2/2001

(Continued)

OTHER PUBLICATIONS

Aase, et al., *Compression Depth Estimation for CPR Quality Assessment Using DSP on Accelerometer Signals*, IEEE Transactions on Biomedical Engineering, vol. 49, No. 3, Mar. 2002.

(Continued)

*Primary Examiner*—Danton DeMille
(74) *Attorney, Agent, or Firm*—K. David Crockett, Esq.; Crockett & Crockett

(57) ABSTRACT

A method of processing a raw acceleration signal, measured by an accelerometer-based compression monitor, to produce an accurate and precise estimated actual depth of chest compressions. The raw acceleration signal is filtered during integration and then a moving average of past starting points estimates the actual current starting point. An estimated actual peak of the compression is then determined in a similar fashion. The estimated actual starting point is subtracted from the estimated actual peak to calculate the estimated actual depth of chest compressions. In addition, one or more reference sensors (such as an ECG noise sensor) may be used to help establish the starting points of compressions. The reference sensors may be used, either alone or in combination with other signal processing techniques, to enhance the accuracy and precision of the estimated actual depth of compressions.

44 Claims, 17 Drawing Sheets

U.S. PATENT DOCUMENTS

| | | | |
|---|---|---|---|
| 6,016,445 | A | 1/2000 | Baura |
| 6,125,299 | A | 9/2000 | Groenke |
| 6,263,238 | B1 | 7/2001 | Brewer |
| 6,306,107 | B1* | 10/2001 | Myklebust et al. ......... 600/587 |
| 6,360,602 | B1 | 3/2002 | Tazartes |
| 6,366,811 | B1 | 4/2002 | Carlson ....................... 607/27 |
| 6,390,996 | B1 | 5/2002 | Halperin et al. |
| 6,411,843 | B1 | 6/2002 | Zarychta |
| 6,453,272 | B1 | 9/2002 | Slechta |
| 6,640,134 | B1 | 10/2003 | Raymond et al. ........... 600/513 |
| 6,647,287 | B1 | 11/2003 | Peel, III et al. ............. 600/513 |
| 2001/0047140 | A1 | 11/2001 | Freeman et al. |
| 2002/0077560 | A1 | 6/2002 | Kramer et al. .............. 600/509 |
| 2004/0087839 | A1* | 5/2004 | Raymond et al. ........... 600/300 |

FOREIGN PATENT DOCUMENTS

| | | |
|---|---|---|
| WO | WO 02/15836 | 2/2002 |

OTHER PUBLICATIONS

Thakor, et al., *Applications of Adaptive Filtering to ECG Analysis: Noise Cancellation and Arrhythmia Detection*, 38 IEEE Transactions on Biomedical Engineering, No. 8, 785-94 (Aug. 1991).

Luo, et al., *Experimental Study: Brachial Motion Artifact Reduction in the ECG*, Computers in Cardiology, 33-6 (Sep. 10-13, 1995).

Eilevstjonn, et al., *Multichannel Adaptive Filtering Using an Efficient Matching Pursuit-Like Algorithm for Removal of CPR Artifacts in ECG Signals*, 4 IEEE International Conference on Acoustics, Speech, and Signal Processing, 3864-67 (May 13-17, 2002).

Husoy, *Removal of Cardiopulmonary Resuscitation Artifacts from Human ECG Using an Efficient Matching Pursuit-Like Algorithm*, IEEE Transactions on Biomedical Engineering, Vo 49, No. 11, Nov. 2002.

Provaznik, et al., *Adaptive Recurrent System for Noise Cancellation and Arrhythmia Detection*, 16th Conference of the IEEE Engineering in Medicine and Biology Society, 1270-1, (Nov. 3-6, 1994).

Pinchak, et al., *Chest Wall Acceleration and Force Measurements in Simulated Manual and Mechanical Cardiopulmonary Resuscitation*, 16 Critical Care Medicine, p. 151-160 (1988).

Pinchak, et al., *Accelerometer Measurements in CPR*, 37 ACEMB, p. 32 (Sep. 17-19 1984).

Gruben, et al., *System for Mechanical Measurements During Cardiopulmonary Resuscitation in Humans*, 37 IEEE Transactions on Biomedical Engineering, p. 204-210 (Feb. 1990).

* cited by examiner

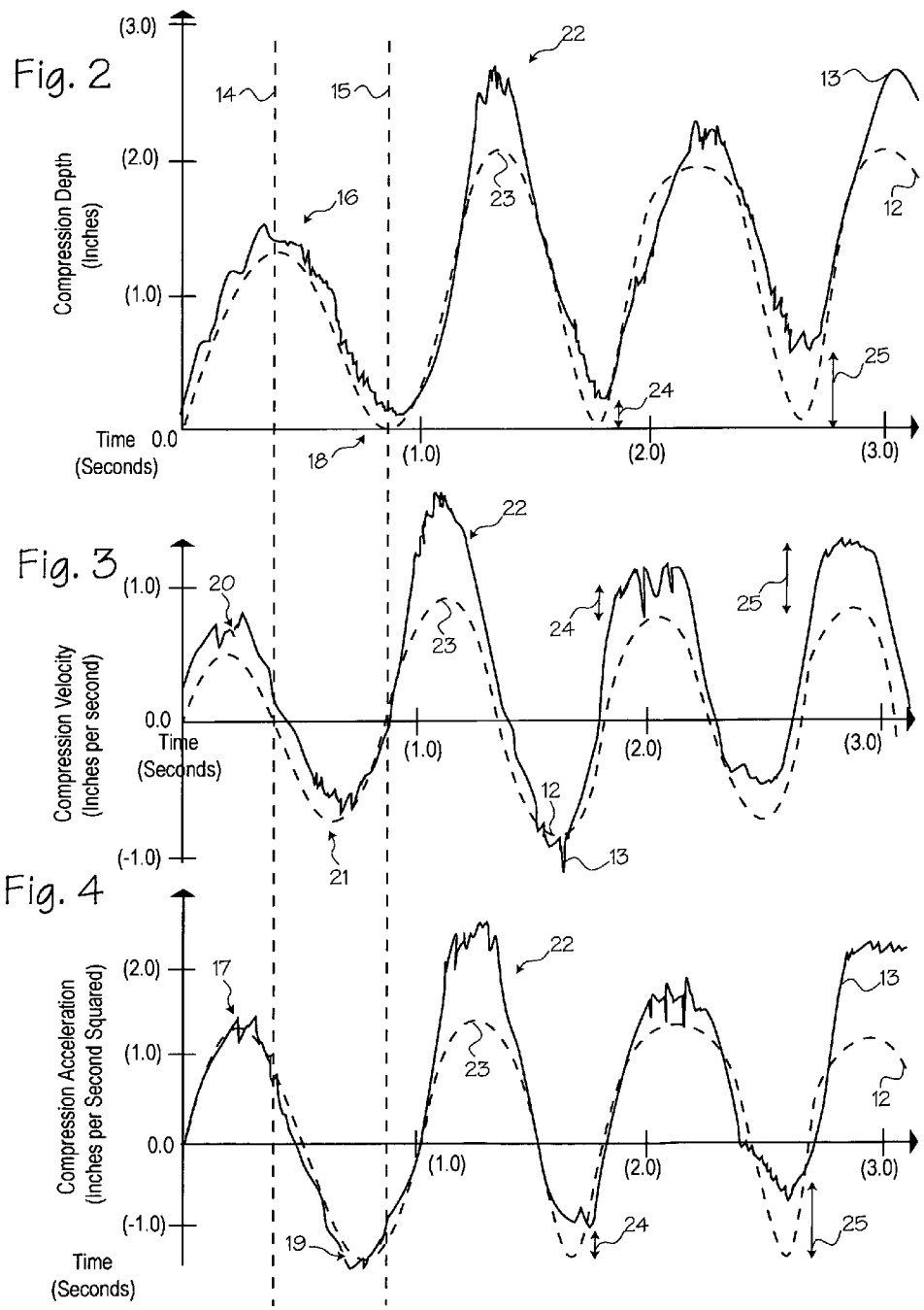

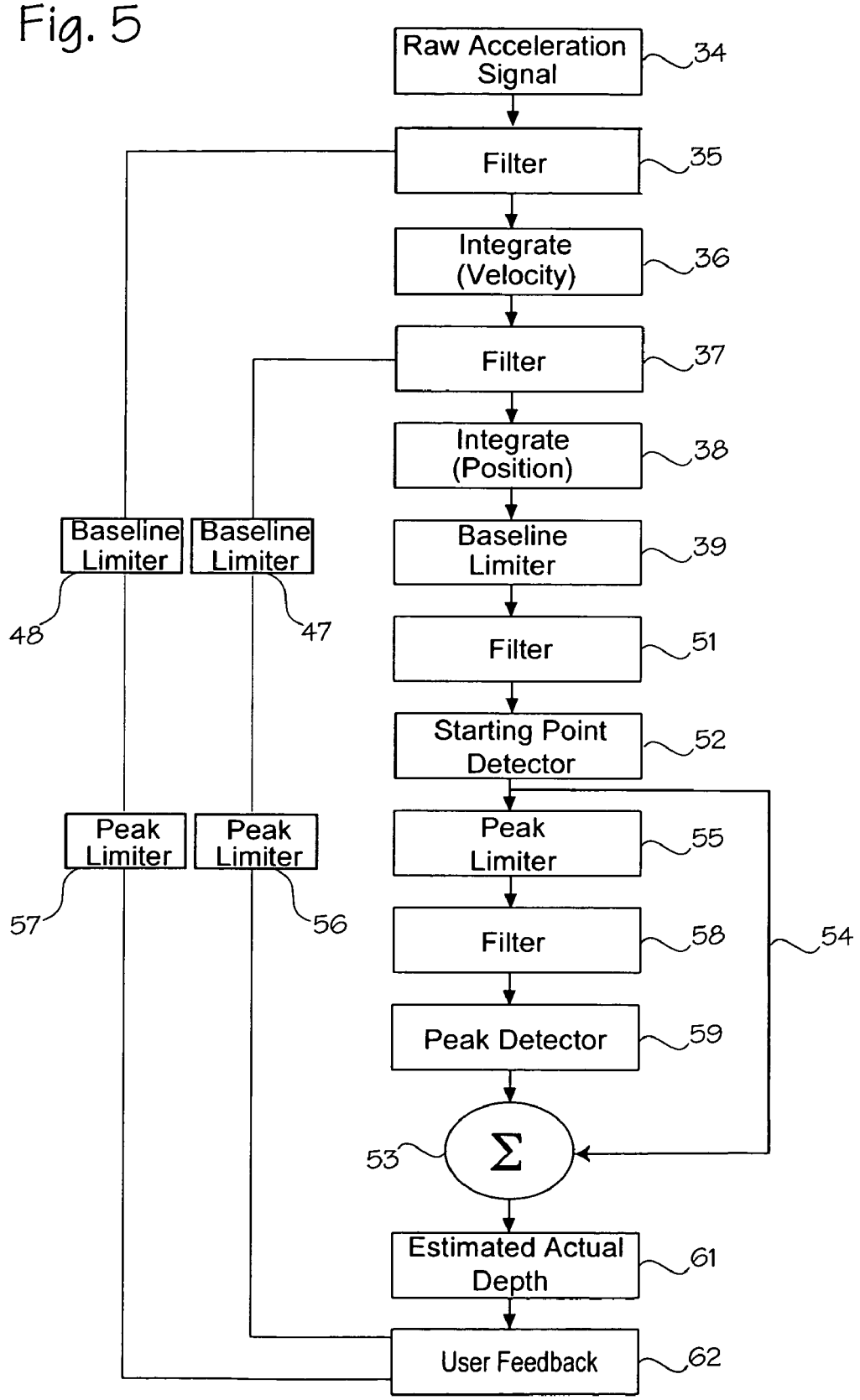

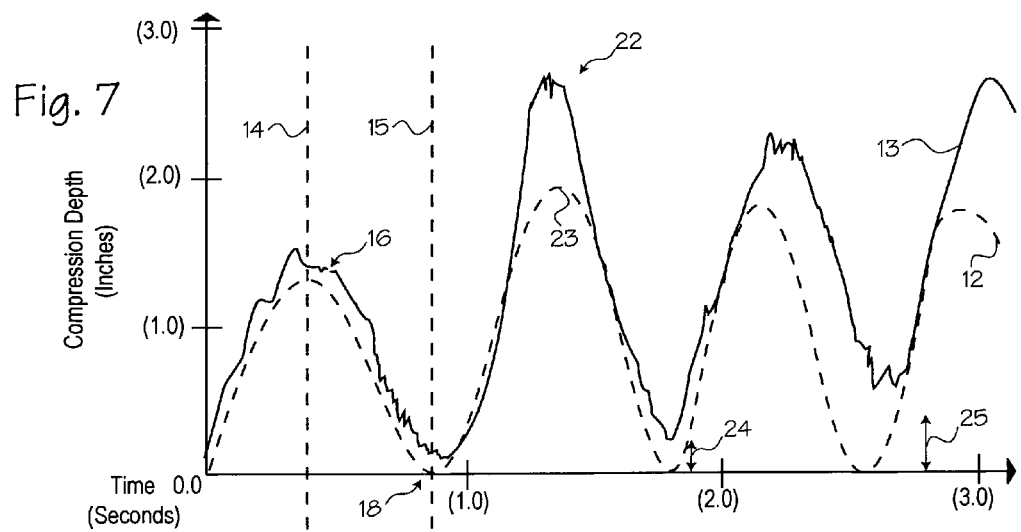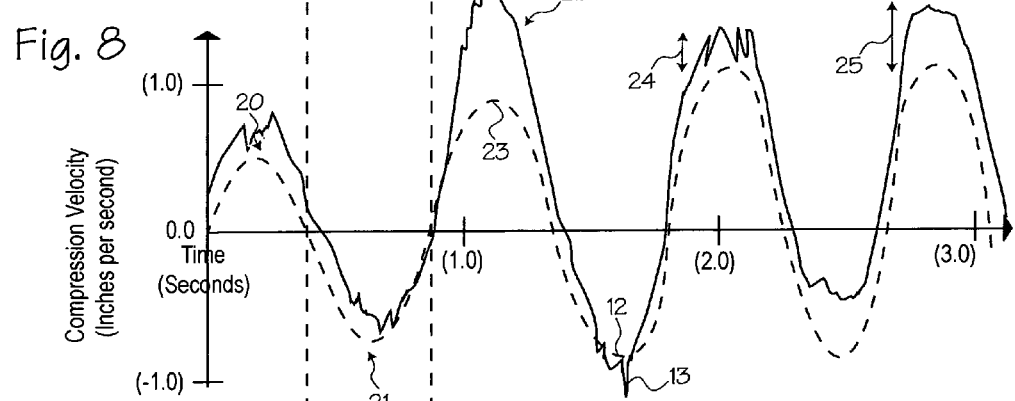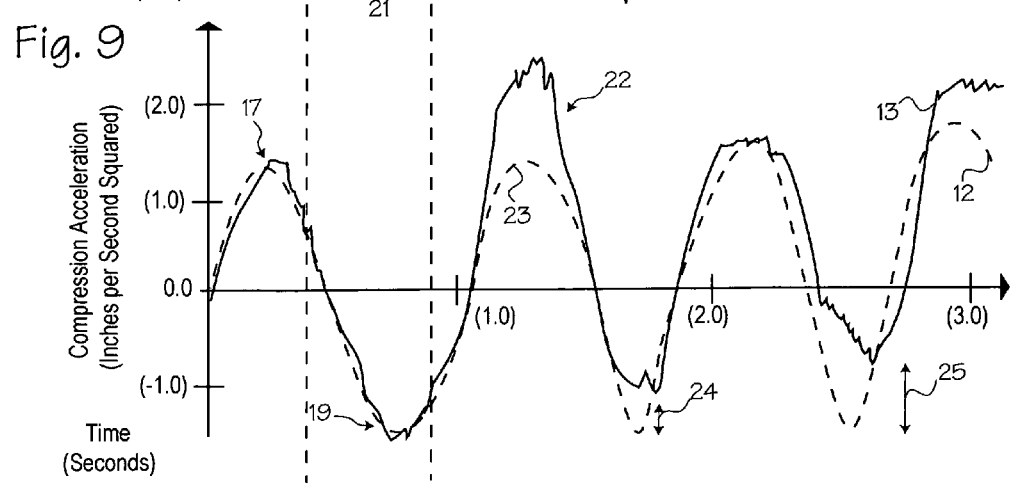

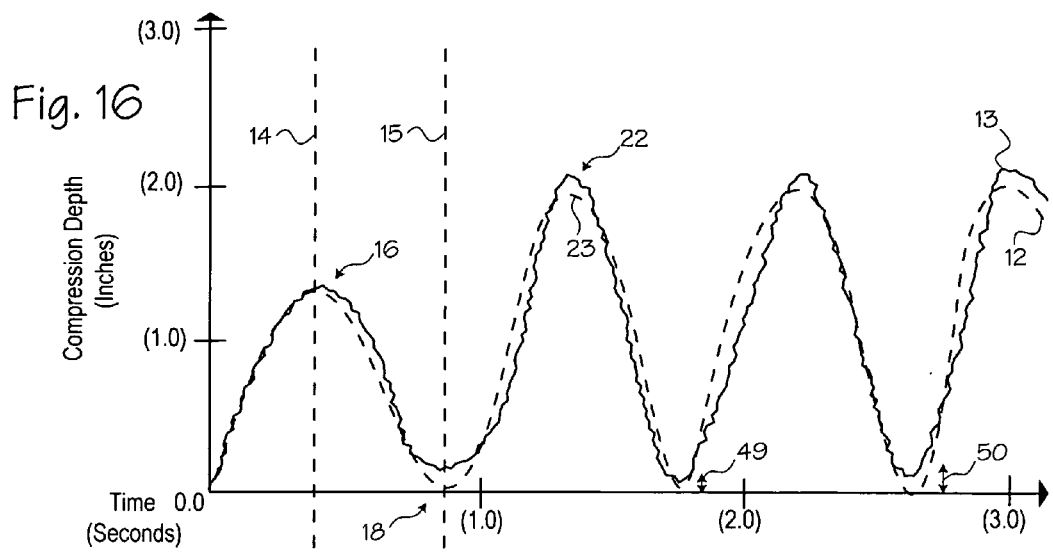
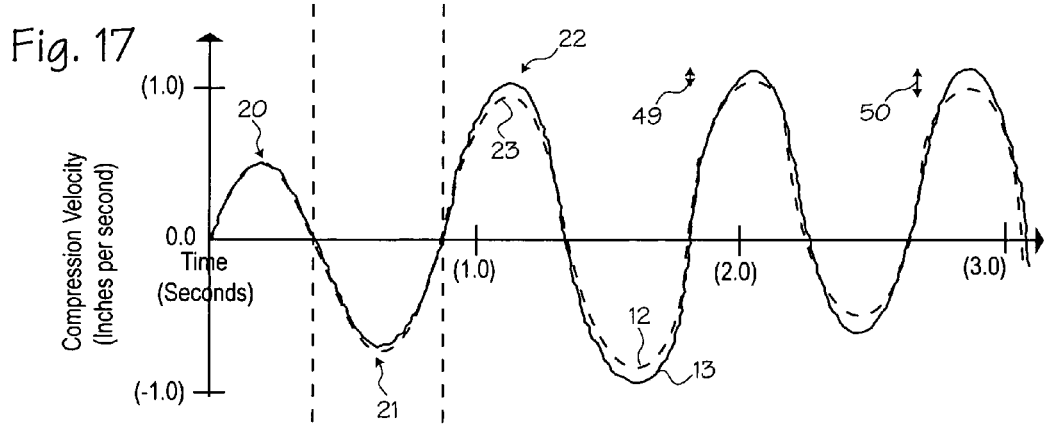
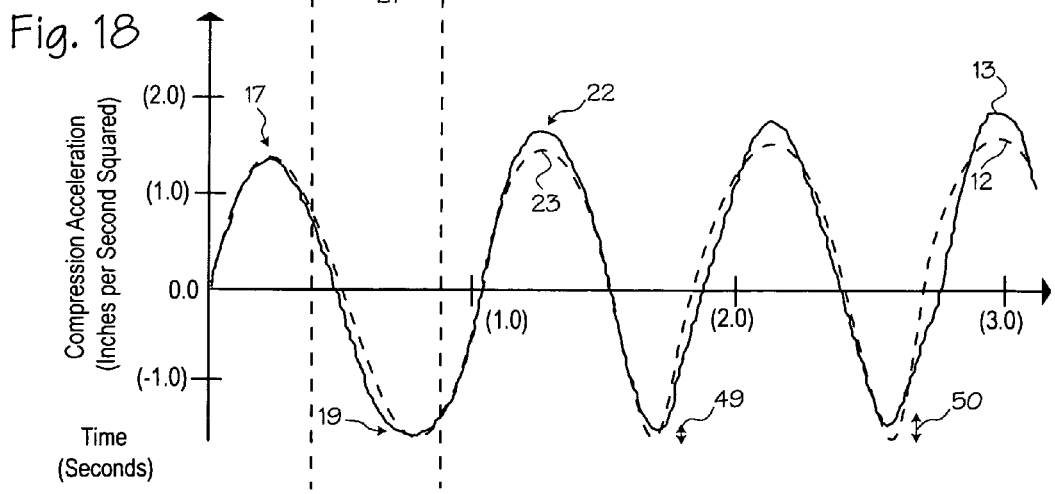

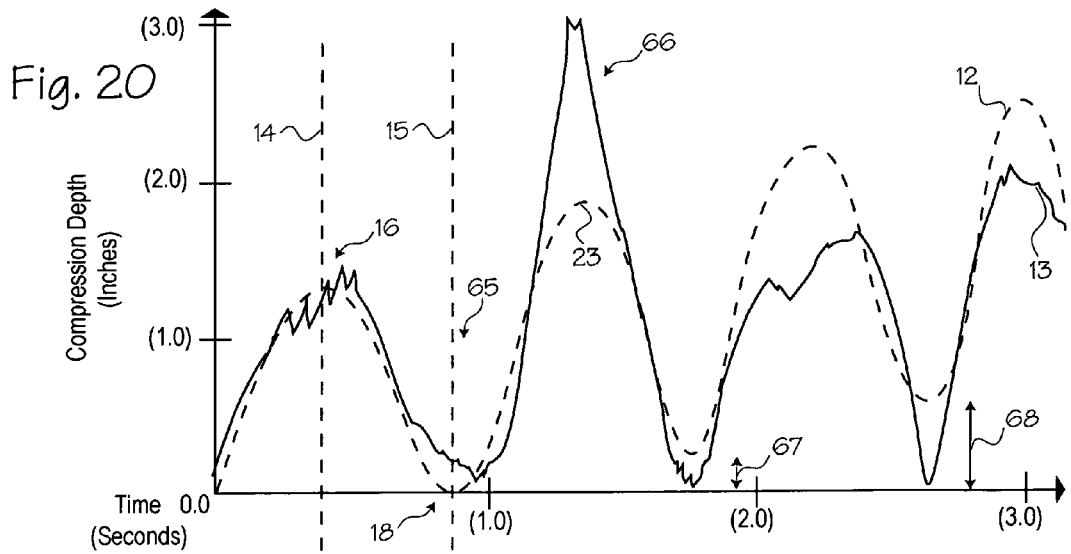
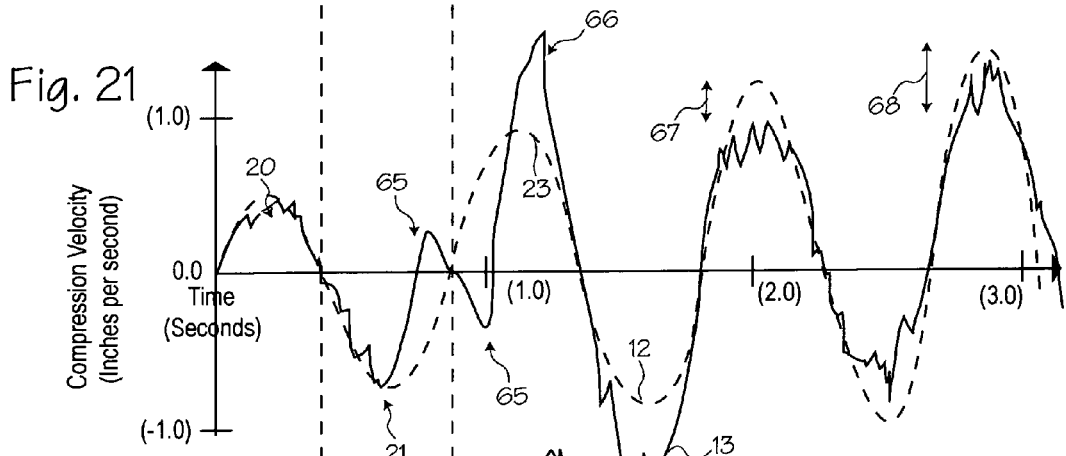
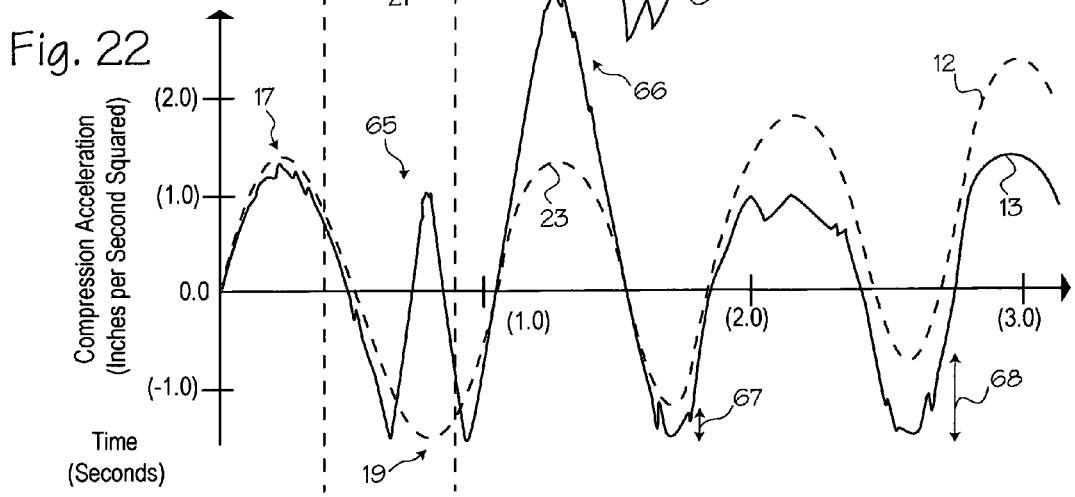

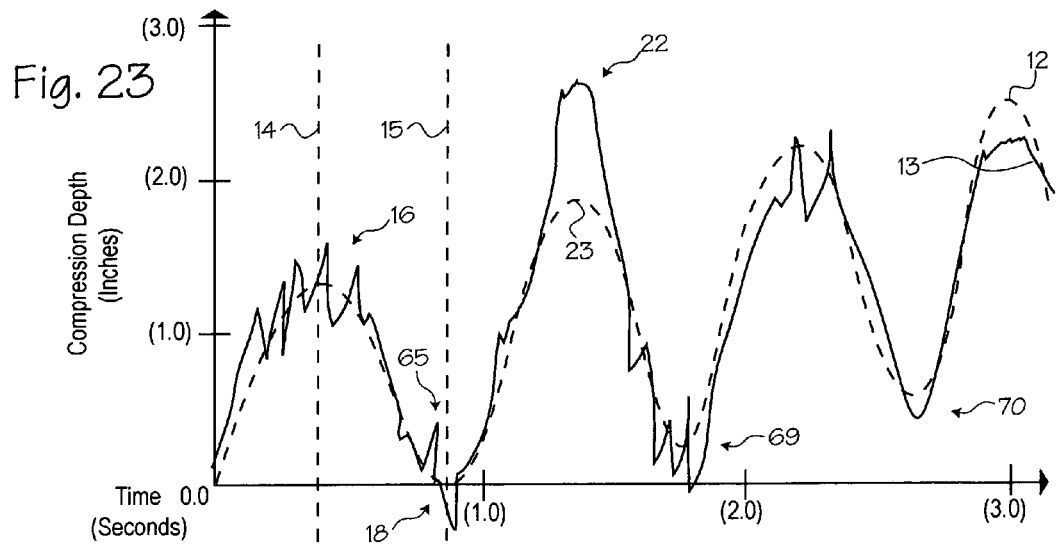
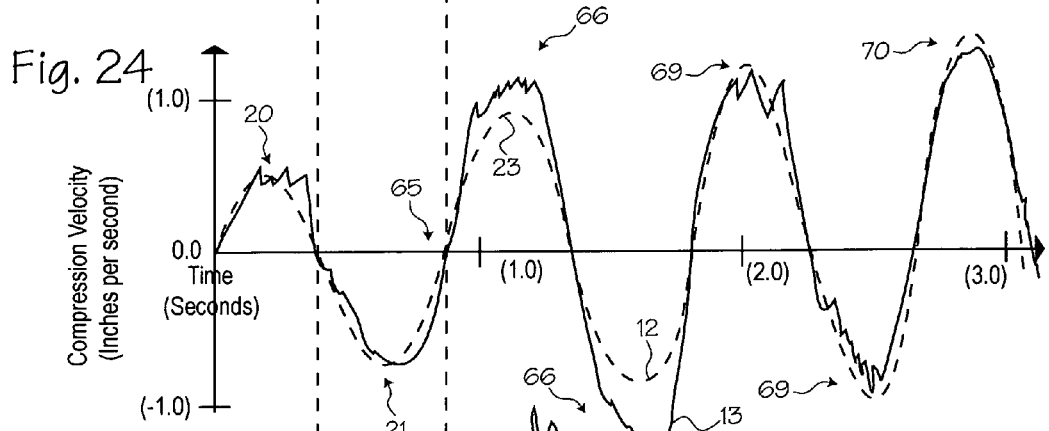
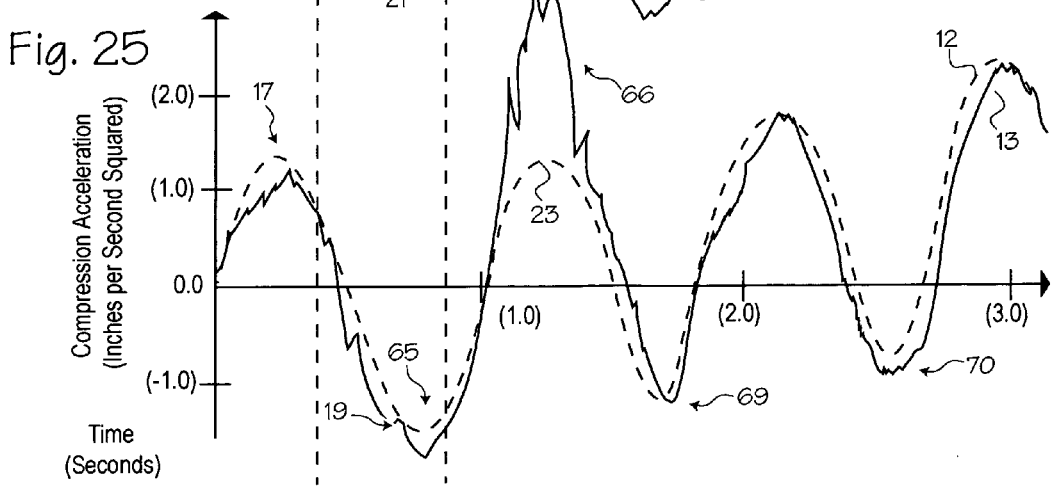

DEVICES FOR DETERMINING DEPTH OF CHEST COMPRESSIONS DURING CPR

This application is a continuation of U.S. application Ser. No. 10/280,220 filed Oct. 25, 2002, now U.S. Pat. No. 6,827,695.

FIELD OF THE INVENTIONS

The methods and devices described below relate to the field of cardio-pulmonary resuscitation (CPR).

BACKGROUND OF THE INVENTIONS

The American Heart Association guidelines for the correct application of cardio-pulmonary resuscitation (CPR) specify that chest compressions be performed at the rate of 80 to 100 per minute and at a depth, relative to the spine, of 1.5 to 2.0 inches. (Guidelines 2000 for Cardiopulmonary Resuscitation and Emergency Cardiovascular Care, 102 Circulation Supp. I (2000).) However, CPR is physically and emotionally challenging, even for trained professionals. Research has shown that manual chest compressions rarely meet the guidelines. See, for example, Ochoa et al., *The Effect of Rescuer Fatigue on the Quality of Chest Compressions, Resuscitation*, vol. 37, p.149–52. See also Hightower et al., *Decay in Quality of Closed-Chest Compressions over Time, Ann Emerg Med*, 26(3):300–333, September 1995. One of the difficulties of performing correct chest compressions is that the rescuer imprecisely judges the timing and depth of compressions, particularly when the rescuer becomes tired. Thus, if accurate and timely user feedback could be provided to the rescuer then the rescuer would be more likely to perform CPR correctly.

Various devices have been proposed to assist a rescuer in properly applying CPR. For example, Kelley, *Apparatus for Assisting in the Application of Cardiopulmonary Resuscitation*, U.S. Pat. No. 5,496,257 (Mar. 5, 1996) shows a device that uses a pressure sensor to monitor compression forces and timing. Groenke et al., *AED with Force Sensor*, U.S. Pat. No. 6,125,299 (Sep. 26, 2000) shows a device that uses a force sensor to measure the compression force applied to a patient's chest. However, these devices only measure the force applied to the chest and do not measure the actual depth of compressions. A given force can compress the chests of different patients by different amounts, so measuring only force will not provide sufficient or consistent feedback to the rescuer. In addition, force-based measurements may also be inaccurate because of intra-patient variation in thoracic morphology and compliance (stiffness).

CPR devices that use only accelerometers to measure depth of compressions, other than our own patented device shown in Halperin et al., *CPR Chest Compression Monitor*, U.S. Pat. No. 6,390,996 (May 21, 2002), do not fully or accurately account for errors in the measured acceleration; nor do they account for drift in the starting points of compressions. In addition, the integration process necessary to derive the depth of compressions greatly compounds any errors in the measured acceleration.

It is important to correct for errors in the measured acceleration since the total depth of compressions should be within the relatively narrow range of 1.5 inches to 2.0 inches. Numerical simulations have shown that a total error in acceleration as small as 0.02 in/sec$^2$ results in an error of 0.25 inches in displacement. Given the narrow depth range of optimal compressions, an error of 0.25 inches is unacceptable. For example, Freeman, *Integrated Resuscitation*, U.S. Publication 2001/0047140 (Nov. 29, 2001) shows a device that uses an accelerometer as a compression sensor and mentions gauging chest depth with the accelerometer. However, Freeman enables no method to account for the errors inherent in using an accelerometer alone. Thus any measurement Freeman makes of chest compression depth is inaccurate.

Myklebust et al., *System for Measuring and Using Parameters During Chest Compression in a Life-Saving Situation or a Practice Situation and Also Application Thereof*, U.S. Pat. No. 6,306,107 (Oct. 23, 2001) describes a device which uses a pressure pad, containing an accelerometer and a force activated switch, to determine the depth of depressions. However, Myklebust does not provide a means to measure compression depth using an accelerometer alone, nor does Myklebust account for some kinds of error in the measured value of chest compression depth (such as drift).

The problems inherent in the above devices show the difficulty of solving the problem of measuring chest compression depth using only an accelerometer. Nevertheless, the basic concept of determining displacement from a measured acceleration is straightforward (in a system with a known starting position). Displacement is determined by double integrating the measured acceleration.

However, this method of measuring chest compression depth is complicated by at least three major sources of error: signal error, external acceleration error, and drift in the actual or measured starting points of compressions from the initial starting point of compressions. Signal error comprises errors in the measured acceleration due to electronic noise, the shaking of wires or cables, errors inherent in the accelerometer, and other sources of noise in the acceleration itself.

External acceleration error comprises errors introduced by accelerations applied to the patient and/or the accelerometer other than accelerations caused by CPR. For example, if the patient is being transported in an ambulance and a rescuer is applying manual CPR with a compression monitor, then the accelerometer will measure accelerations caused by road vibrations as well as accelerations caused by CPR. (If the ambulance hits a pot hole then a large spike may appear in the compression waveform.) The accelerometer, by itself, cannot distinguish between the accelerations caused by road noise and the accelerations caused by compressions. In other words, the accelerometer measures a combined acceleration and not just the accelerations caused by compressions. Accordingly, the compression monitor will report a displacement value different from the actual chest displacement.

Another source of error, drift, comprises systematic shifts in the actual or reported starting points of each compression over an entire series of compressions. The accelerometer has no "memory" of the initial starting position. Thus, as the rescuer applies compressions the reported depth waveform can start to drift. The compression monitor may indicate that the reported depth waveform is increasingly deeper than the actual waveform. This form of drift is referred to as positive drift. On the other hand, drift can also cause the compression monitor to report a depth waveform that is increasingly more shallow than the actual waveform. In other words, actual compression starting points are becoming increasingly deeper, but the compression monitor instead reports each starting point as close to the initial starting point. This form of drift is referred to as negative drift.

One cause of negative drift is a failure to allow the chest to return to a fully relaxed position. Absent correction, the accelerometer will begin measuring displacement from the new "initial" position. Thus, the compression monitor erroneously informs the rescuer that the current starting point is at the initial starting point. However, the actual depth of the current starting point is more than the depth reported by the compression monitor. As a result, the rescuer may compress the chest harder than he should to achieve the erroneous depth suggested by the compression monitor.

Another source of both types of drift is a change in the overall position of the accelerometer with respect to the patient. For example, if the accelerometer is not fully secured then the accelerometer may systematically slip. (This may also cause external acceleration error.) Yet another source of drift is expansion and contraction of the chest due to ventilation performed simultaneously with compressions. Other sources of drift may also exist. Each source of drift may be independent of the others and may not cancel each other out, so the compression monitor should be able to account for both positive and negative drift.

Notwithstanding drift resulting from erroneous operation, changes in the actual starting point of compressions do occur. For example, if one or more ribs break during CPR then the actual starting point of each compression may be closer to the spine (a phenomena known as chest remodeling). Other types of chest injury or disease that affect the structure and strength of the rib cage can also cause chest remodeling. Chest remodeling can be gradual, in which case a gradual shift occurs in the actual initial starting point of compressions. A compression monitor should be able to account for the difference between erroneous drift and an actual shift in the starting points of compressions.

These and other sources of error are compounded by integrating the acceleration. The errors caused by signal noise and drift cause the constants of integration to have a value other than zero. The non-zero constants of integration compound the errors already present in the acceleration. Thus, the total compression depth reported by the compression monitor can be very inaccurate. Accordingly, methods are needed to accurately and precisely derive the depth of chest compressions from a measured acceleration.

SUMMARY

The methods and devices described below provide for signal processing techniques that precisely and accurately derive the depth of chest compressions from a measured acceleration of chest compressions. Specifically, the methods and devices provided below provide for a means to correct chest displacement errors caused by signal error, external acceleration error, and drift. According to one method, a moving average technique is used to produce an accurate measurement of compression depth. According to a second method, a change in the patient's ECG (electrocardiogram) may be used to determine the starting points of compressions. These methods may be combined together to further increase the accuracy of chest depth measurement.

In broad terms, a moving average technique averages a plurality of compression cycles together, but weights recent compressions more heavily than compressions further in the past. One moving average technique begins with filtering a raw acceleration signal to eliminate as much signal noise as practicable. The filtered acceleration signal is then integrated to derive the velocity of compressions. The velocity is filtered to remove accumulated low frequency variations. The filtered velocity measurement is integrated again to derive chest displacement. Chest displacement is then processed through a baseline limiter and a peak limiter; the baseline limiter may comprise a moving average processor and the peak limiter may comprise a moving average processor. The baseline limiter estimates the actual starting point of the current compression and the peak limiter estimates the actual peak depth of the current compression. A baseline detector then identifies the starting point of the current compression. A peak detector then identifies the peak depth of the current compression. A means for combining signals then combines the estimated starting point and the estimated peak depth to derive the estimated actual depth of the current compression. Finally, the estimated actual depth of the current compression is provided to one or more devices which provide intelligible feedback to a manual CPR provider, to an automated CPR device, or to an ECG operator.

In another method, a change in the noise component of the patient's ECG is correlated to the start of a chest compression. When the noise component of the patient's ECG signal exceeds a pre-determined threshold then the accelerometer begins to measure acceleration. Thus, the actual starting point of the current compression is established. This method reduces some forms of external acceleration error and reduced drift. The method also helps to set the constants of integration to zero.

BRIEF DESCRIPTION OF THE DRAWINGS

FIG. 2 shows a graph of compression depth over time before signal processing, where compression depth is derived from a measured acceleration.

FIG. 3 shows a graph of compression velocity over time before signal processing, where compression velocity is derived from a measured acceleration.

FIG. 4 shows a graph of compression acceleration over time before signal processing, where compression acceleration is measured by an accelerometer.

FIG. 5 is a flow chart of a signal processing technique that converts a raw compression acceleration into an estimated actual compression depth.

FIG. 7 shows the graph of compression depth over time after filtering the raw acceleration.

FIG. 8 shows the graph of compression velocity over time after filtering the raw acceleration.

FIG. 9 shows the graph of compression acceleration over time after filtering the raw acceleration.

FIG. 16 shows the graph of compression depth over time after filtering both the raw acceleration and the derived velocity, and after applying the baseline limiter and the peak limiter to the compression depth waveform.

FIG. 17 shows the graph of compression velocity over time after filtering both the raw acceleration and the derived velocity, and after applying the baseline limiter and the peak limiter to the compression velocity waveform.

FIG. 18 shows the graph of compression acceleration over time after filtering the raw acceleration and after applying the baseline limiter and the peak limiter to the compression acceleration waveform.

FIG. 20 shows a graph of compression depth over time before signal processing and with a negative drift in the reported compression depth waveform.

FIG. 21 shows a graph of compression velocity over time before signal processing and with a negative drift in the reported compression velocity waveform.

FIG. 22 shows a graph of compression acceleration over time before signal processing and with a negative drift in the reported compression acceleration waveform.

FIG. 23 shows the graph of FIG. 20 corrected by using a change in ECG noise to establish the actual starting points of compressions.

FIG. 24 shows the graph of FIG. 21 corrected by using a change in ECG noise to establish the actual starting points of compressions.

FIG. 25 shows the graph of FIG. 22 corrected by using a change in ECG noise to establish the actual starting points of compressions.

DETAILED DESCRIPTION OF THE INVENTIONS

Figure 1:
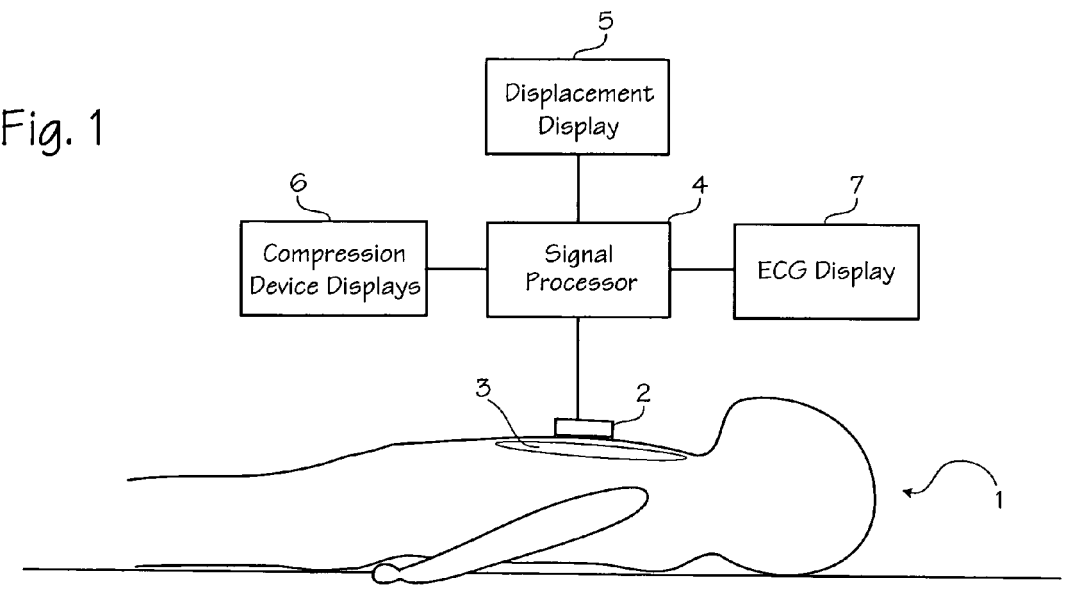
FIG. 1 shows a patient and an accelerometer-based compression monitor in place on a patient.

FIG. 1 shows a patient 1 and an accelerometer-based compression monitor 2 in place on the patient. An accelerometer-based compression monitor uses one or more accelerometers to determine the depth of compressions. An example of an accelerometer-based compression monitor may be found in our own patent, Halperin et al., *CPR Chest Compression Monitor*, U.S. Pat. No. 6,390,996 (May 21, 2002), which is hereby incorporated by reference in its entirety. The compression monitor 2 is placed on the sternum 3 of the patient 1, on the rescuer's hands or arms, or on an automatic CPR device. The chest is then compressed. The accelerometer measures the acceleration of compressions and a processor 4 estimates the actual displacement of the accelerometer based on the measured acceleration. The signal processing techniques described below ensure that the estimated actual displacement is accurate and precise.

The estimated actual displacement may be provided to a displacement display 5 that provides intelligible feedback to a manual CPR provider or to an automated CPR device. Likewise, other CPR-related parameters may be provided to one or more compression device displays 6 (or other means for user feedback). CPR-related parameters include the depth of chest compressions, the velocity of chest compressions, the acceleration of chest compressions, and the patient's ECG.

In the case of the patient's ECG, the compression monitor may be provided with one or more electrodes. The processor may process the patient's ECG during compressions to produce an estimated actual ECG. The estimated actual ECG may then be provided to an ECG display 7 (or other means for user feedback) that provides intelligible feedback to the manual CPR provider, to an automated CPR device, or to other individuals or devices that monitor the patient's ECG.

The following terms are used throughout the specification and are defined as follows:

Actual compression depth: the actual depth of a compression at any given time.

Actual starting point of a compression: the actual place or point at which a chest compression begins.

Autoregressive moving average: a function that uses past data samples to modify the current data sample.

Baseline portion of the compression depth waveform: that portion of depth waveform where the set of actual starting points is most likely to be found.

Baseline limiter: a processor or function that operates on the baseline portion of the compression depth waveform.

Compression Peak: the place or point where maximum compression depth occurs.

Current compression depth: the depth of a compression at any given time.

Current starting points: the starting point of the current compression.

Depth of compressions: the depth the chest is compressed at any instant in time, where depth is measured relative to the relaxed position of the chest.

Estimated actual starting point of a compression: the estimated value of the actual place or point at which a chest compression begins.

Initial starting point of compressions: the place or point at which a series of compressions begins.

Measured starting point of a compression: the measured value of the place or point at which a chest compression begins.

Moving average: a function that uses past data samples to modify the current data sample.

Past starting points: the starting points of compressions that have already occurred.

Peak portion of the compression depth waveform: that portion of depth waveform where the set of actual peaks are most likely to be found.

Starting point of a compression: the place or point at which a chest compression is begun.

FIGS. 2 through 4 show graphs of compression depth, velocity, and acceleration over time for four hypothetical compressions. No signal processing has been applied to any of waveforms shown in FIGS. 2 through 4. Compression depth in FIG. 2 is shown as a positive value—the higher the value, the deeper the chest has been compressed. The phantom waveforms 12 represent the actual waveforms for compression depth, velocity, and acceleration (measured independently of the accelerometer). The solid waveforms 13 represents the waveforms derived from the acceleration measured by the compression monitor accelerometer. The waveforms 13 are also the waveforms reported by the compression monitor to the signal processing system 4. Compression depth is measured in inches, marked at 1 inch intervals, compression velocity is measured in inches per second (in/s), marked at 1 in/s intervals, and compression acceleration is measured in inches per second per second (in/s$^2$), marked at 1 in/s$^2$ intervals. For all three Figures time is measured in seconds, marked at 1 second intervals. The start of compressions is at time equal to zero. The initial depth of compressions is at depth equal to zero.

Phantom lines 14 and 15 intersect all three graphs. Phantom line 14 corresponds to the time at which maximum compression depth is obtained. Phantom line 15 corresponds to the time at which minimum compression depth is obtained. In addition, phantom line 14 indicates that a compression depth maximum 16 corresponds to a compression velocity of zero. Phantom line 14 also indicates that an acceleration maximum 17 is slightly offset from the compression depth maximum 16. Likewise, phantom line 15 indicates that a compression minimum 18 (or starting point or zero point) corresponds to a compression velocity of zero. Phantom line 15 also indicates that an acceleration minimum 19 is slightly offset from the compression depth minimum 18. A compression velocity maximum 20 and minimum 21 occur around the middle of a compression.

The solid waveforms show the effects of three major types of error: signal error, external acceleration error, and drift. Signal error is primarily represented by the "noisy" (rough) nature of the solid waveforms; however, external acceleration error can also form a portion of the "noise." Although the acceleration waveform is less noisy, integrating the acceleration increases the effect of the noise in the velocity waveform. Integrating the velocity waveform increases the effect of the noise yet again. Thus, the compression depth noise FIG. 2 is higher than the compression velocity noise in FIG. 3, which is in turn higher than the compression acceleration noise in FIG. 4. Accordingly, the compression monitor will report a very noisy compression depth waveform.

External acceleration error is primarily represented by the large, positive spike 22 in the solid waveforms of FIGS. 2 through 4. (Although the spike in FIGS. 2 through 4 occurs at a maximum, spikes can occur anywhere in the compression cycle and can affect the measured acceleration both positively and negatively). The spike is caused by a large acceleration unrelated to compressions, but nevertheless measured by the accelerometer. Thus, the actual waveform 12 in all three figures shows a corresponding peak 23 significantly below spike 22. Accordingly, absent the correction suggested here, the compression monitor will report for that compression cycle a compression depth much higher than the actual compression depth.

Drift is primarily represented by the increasing distance between the respective minimums of the actual and reported waveforms of FIGS. 2 through 4, as shown by arrows 24 and 25. The drift is causing the compression monitor to erroneously report a compression waveform that is becoming increasingly deeper (positive drift). However, the actual waveform is more closely returning to the initial starting point, and is thus the drift shown in FIGS. 2 through 4 is considered a positive drift. Likewise, arrows 24 and 25 in FIGS. 3 and 4 illustrate that drift has an increasing affect on the reported velocity and the reported acceleration. The effects of drift mean that the initial starting point of compressions cannot be used as a reliable starting point for all compressions. Accordingly, the starting point of compressions must be determined for every compression cycle. In addition, the other sources of noise must be either eliminated or greatly reduced.

FIG. 5 is a flow chart of a signal processing technique that converts a raw acceleration into an estimated actual value for total compression depth. The raw acceleration 34 is filtered by a first filter in step 35 to produce a filtered acceleration. The first filter comprises a high-pass filter and greatly reduces most forms of signal noise. (In other embodiments the first filter may comprise a band pass filter, a moving average filter, an infinite impulse response filter, an autoregressive filter, or an autoregressive moving average filter.) The effects of the other steps shown in FIG. 5 are described in the context of FIGS. 7 through 18.

Figure 6:
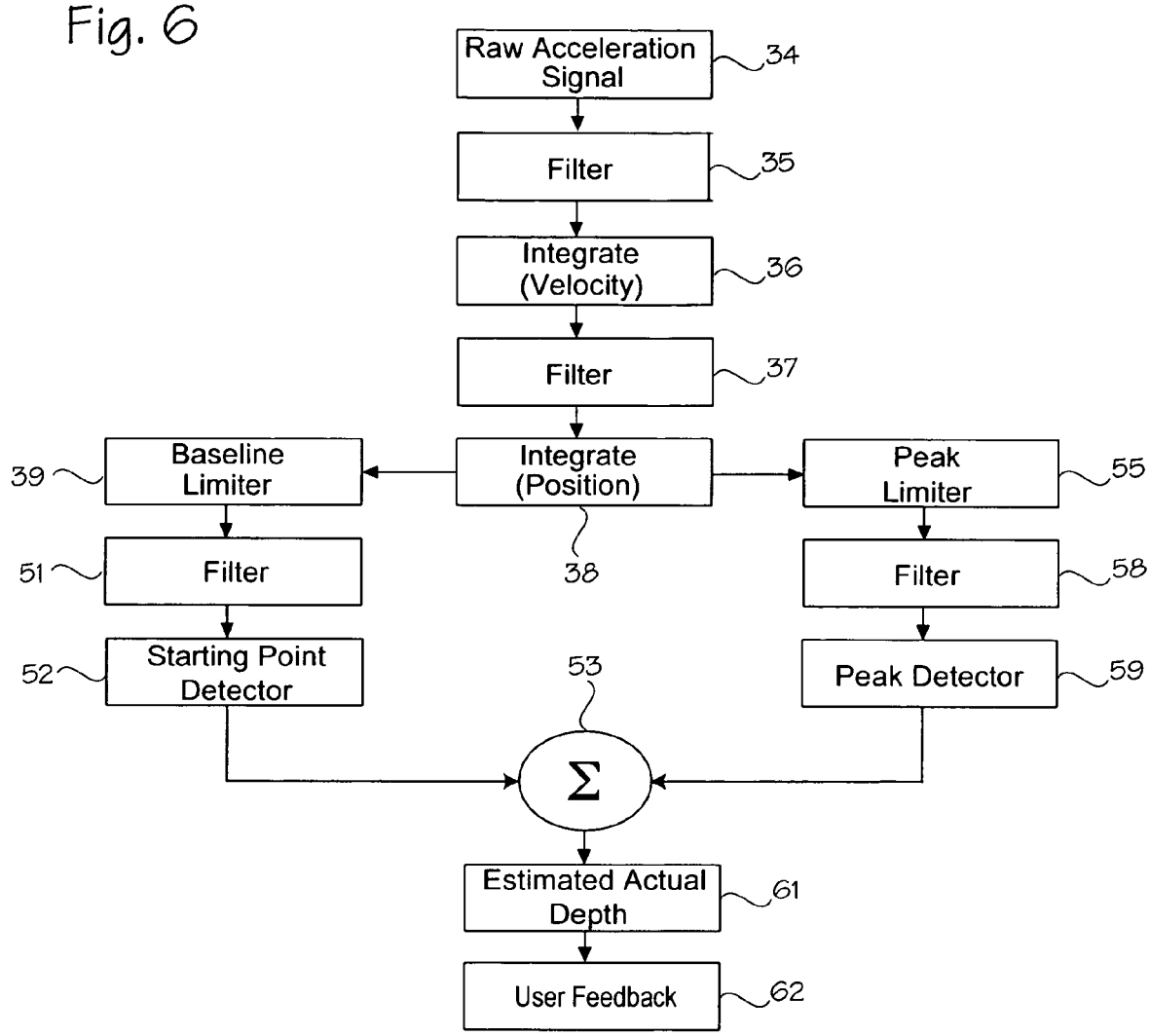
FIG. 6 is a flow chart of an alternate signal processing technique that converts a raw compression acceleration into an estimated actual compression depth.

FIG. 6 is a flow chart of an alternate signal processing technique that converts a raw compression acceleration into an estimated actual compression depth. This flowchart is described after the description for FIGS. 7 through 18.

The effect of the filter operation 35 is seen in FIGS. 7 through 9, which show the graphs of compression depth, velocity, and acceleration over time for four hypothetical compressions after the first filtering step 35. (FIGS. 7 through 9 show the output of the first filtering step). The measured acceleration waveform 13 of FIG. 9 is much less noisy than the corresponding unfiltered waveform 13 of FIG. 4. Since the velocity and depth waveforms of FIGS. 8 and 9 are derived from the acceleration waveform they, too, are less noisy. Nevertheless, the integration process still causes the velocity waveform to be more noisy than the acceleration waveform and the depth waveform to be more noisy than the velocity waveform. In addition, the external acceleration spike 22 still remains, as do the errors caused by drift (as shown by arrows 24 and 25).

Returning to FIG. 5, the filtered acceleration is integrated in a first integration step 36 to derive the compression velocity. However, as shown in FIG. 8, without further processing the velocity waveform is still noisy. Thus, the velocity is filtered by a second filter in step 37 to produce a filtered velocity. The second filter comprises a high pass filter and further reduces most signal noise in the velocity and depth waveforms. (In other embodiments the second filter may comprise a band pass filter, a moving average filter, an infinite impulse response filter, an autoregressive filter, or an autoregressive moving average filter.)

Figure 10:
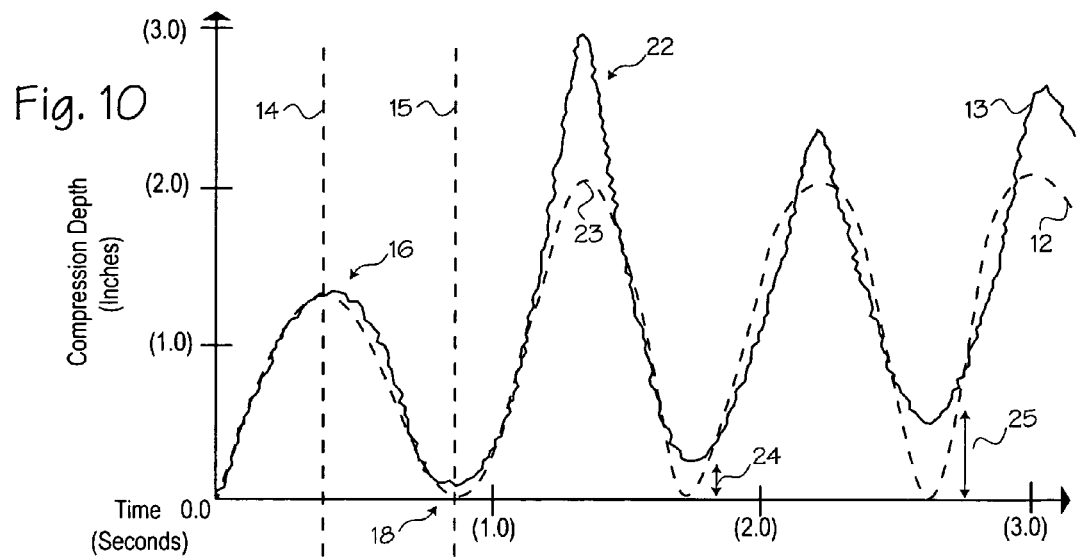
FIG. 10 shows the graph of compression depth over time after filtering both the raw acceleration and the derived velocity.
Figure 11:
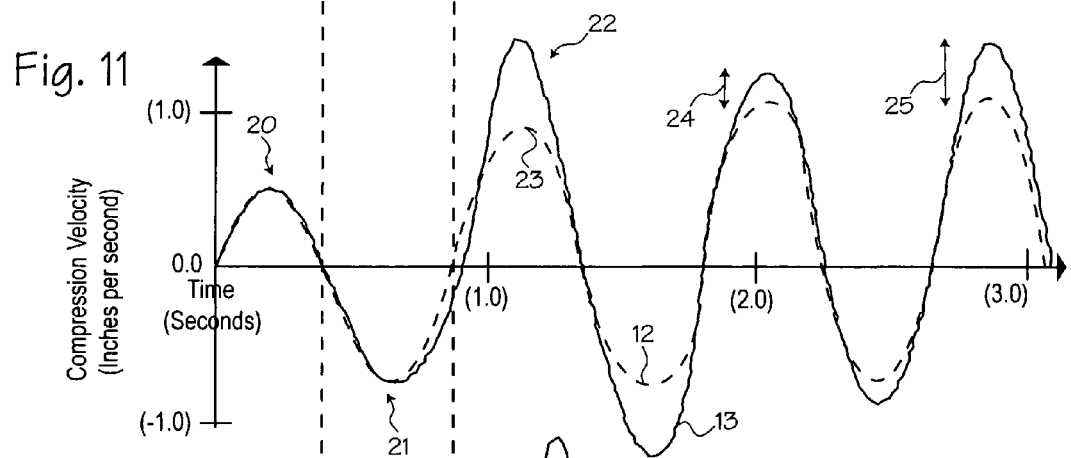
FIG. 11 shows the graph of compression velocity over time after filtering both the raw acceleration and the derived velocity.
Figure 12:
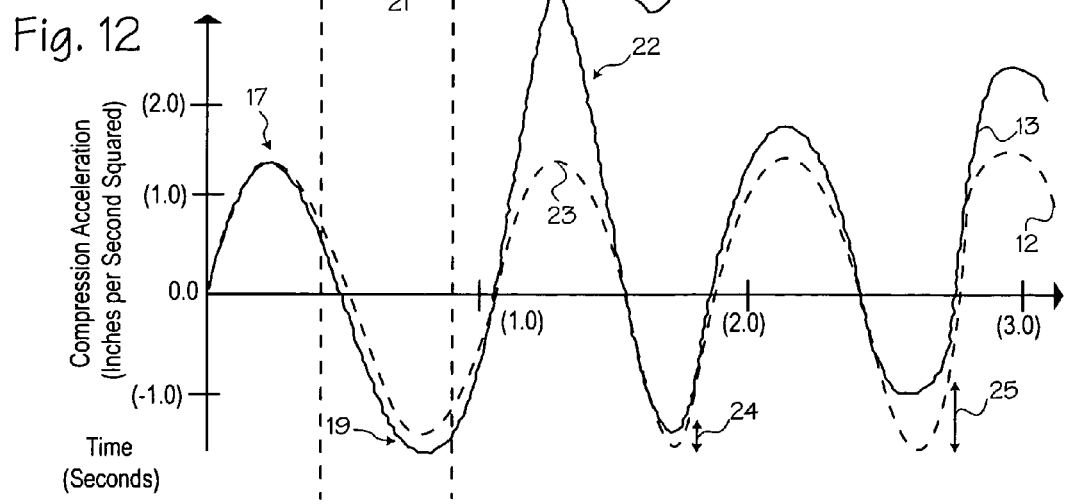
FIG. 12 shows the graph of compression acceleration over time after filtering the raw acceleration.

The effects of the filter operation 37 is seen in FIGS. 10 through 12, which show the graphs of compression depth, velocity, and acceleration over time for four hypothetical compressions after the second filtering step 37. (FIGS. 10 through 12 show the output of the second filtering step 37.) The measured velocity waveform 13 of FIG. 11 is less noisy than that of FIG. 8 (the velocity waveform after the first filtering step). Since the depth waveform is derived from the velocity waveform it, too, is correspondingly less noisy. Nevertheless, the integration process still causes the depth waveform to be slightly more noisy than the acceleration and velocity waveforms. In addition, the external acceleration spike 22 still remains, as do the errors caused by drift (as shown by arrows 24 and 25).

Returning to FIG. 5, the filtered velocity is integrated in a second integration step 38 to calculate the chest compression depth. Signal noise has been substantially eliminated and thus a third filtering step is not required. However, the noise in the depth waveform, as shown in FIG. 10, is still slightly more than the noise in the velocity waveform, as shown in FIG. 11. Thus in other embodiments a third filter, comprising a high pass, bandpass, or other filter may be used to further reduce signal noise in the depth waveform.

After the initial filtering steps (35 and 37) and integration steps (36 and 38), a baseline limiter estimates the actual starting point of a compression in step 39. The baseline limiter uses, among other techniques described below, the starting points from past compressions to estimate the current compression starting point. The baseline limiter itself comprises a digital or analog signal processor that operates on the baseline portion of the compression depth waveform of FIG. 10. The baseline portion of the compression depth waveform comprises that portion of depth waveform where the set of actual starting points is most likely to be found. For example, the baseline may comprise the portion of the depth waveform that is equal to and below 1.1 inches compression depth. (Larger changes in the starting points of compressions are unlikely, and signals indicating large changes are probably wrong.) Thus, the limiter will disregard or arbitrarily assign a realistic depth value to any "starting point" above 1.1 inches depth. In one embodiment, past starting points above the baseline are disregarded and a current starting point above the baseline is reported or treated as an error. (Past starting points are the starting points of compressions that have already occurred. A current starting point is the starting point of the current compression.) In another embodiment a current starting point above the baseline is assigned a small probability and averaged with the past starting points.

In one embodiment the baseline limiter estimates the starting point of the current compression by applying a moving average to all starting points that fall within the baseline portion of the depth waveform. A moving average is a function that uses past data samples to modify the current data sample. (Additional moving average techniques are described below.) In the case of the baseline limiter, the baseline limiter may weigh recent starting points more heavily than older starting points, meaning that the weight of a given starting point decays over time. Starting points that fall outside the baseline portion of the depth waveform are given an arbitrary weight or no weight. By applying a moving average to all starting points the baseline limiter reduces the effect of external acceleration error and drift on the current starting point. In other words, the moving average of all starting points will be statistically closer to the current actual starting point than the current measured starting point derived from the integration of the acceleration.

The following example shows an embodiment of a moving average technique. In this embodiment each compression starting point is given a weight of 1.25% of the previous compression starting point. In other embodiments the weighting may comprise a percentage in the range of about 0.1% to about 12.5% (which yields between about 0.3% to about 90% data weighting at the end of about 1 minute). In other words, the measured value of the current starting point (starting point 1) is weighted 100%, the most recent starting point (starting point 2) is weighted 98.75%, the next previous starting point (starting point 3) is weighted 97.5%, the next previous starting point (starting point 4) is weighted 96.25%, etc until all compressions are weighted. Eventually, compressions in the distant past are given no virtually no weight at all. The depth of all the weighted starting points is then averaged. The weighted average of all starting points is treated or reported as the current starting point.

In another embodiment, all compressions after a pre-determined time period (such as about 1 minute to about 15 minutes) are disregarded. Thus, only compressions within the last 1 to 15 minutes are averaged. In another embodiment, all compressions after a pre-determined number of compressions (such as about 5 to about 15) are disregarded.

Continuing the example, in one embodiment the measured values for starting point 1=0.5 inches, starting point 2=1.1 inches, starting point 3=4.0 inches, and starting point 4=0.9 inches. Starting point 3 is outside the baseline portion of the depth waveform (the baseline portion is 1.1 inches and below in this example). Starting points outside the baseline in this example are disregarded, so starting point 3 is disregarded. Thus, the current starting point would be reported as:

$$[(0.5*100\%)+(1.1*98.75\%)+(0.9*96.25\%)]\div 3=0.853$$
inches relative to the initial starting point.

Had starting point 3 been included in the moving average, then the current starting point would have been reported as:

$$[(0.5*100\%)+(1.1*98.75\%)+(4.0*97.5\%)+(0.9*96.25\%)]\div 4=1.615$$
inches relative to the initial starting point.

Stated differently, this value is the estimated actual starting point for the current compression.

Mathematically, the reported value of the current starting point is expressed as:

$$Ds=[\Sigma(DB_i * \omega^{i-1})]n_r$$

where $$DB_i=0 \text{ if } DB_i>B,$$

where Ds is the depth of the current starting point, $n_r$ is the number of starting points remaining after all starting points that exceed the baseline have been disregarded, i is the starting point number (or sum index), DBi is the measured depth of the $i^{th}$ starting point, $\omega$ is the weighting constant, and B is the baseline. Expressed differently, $DB_i * \omega^{i-1}$ is summed from i=1 to $n_r$ and the sum is divided by $n_r$, but if a particular $DB_i$ is greater than B then that $DB_i$ is instead set to zero.

The baseline limiter may perform other functions to further increase the accuracy and precision of the estimated depth of the current starting point. For example, a probability can be assigned to a given change between the current starting point and the immediate previous starting point. (Likewise a probability can be assigned to a given change between the current starting point and the moving average of all previous starting points.) Large changes in starting point may be given less weight than smaller changes. This technique may be referred to as a "weighted moving average" technique.

Continuing the above example, measured depth 1 is treated as having a 100% probability of occurring. Then, the difference between the current starting point (depth 1) and the previous starting point (depth 2) is 1.1 inches−0.5 inches=0.6 inches. The probability of a step of 0.6 inches occurring is assigned to be 97%, based on past experiments. Since the probability is not 100%, the current starting point is not treated as having jumped a full 0.6 inches. Instead, the current starting point is treated as having jumped 0.6*0.97=0.582 inches. Accordingly when calculating the weighted moving average depth 2 is treated as being 1.082 inches and not 1.1 inches. Starting point 3 is still disregarded. The difference between starting point 2 (1.1 inches) and starting point 4 (0.9 inches) is 0.2 inches, which is assigned a 99% probability. Thus, the effective distance of the step between depth 2 and depth 4 is 0.2*99%=0.198. Accordingly, depth 4 is treated as 0.902 inches instead of 0.9 inches. Using the same moving average as above, the current starting point is now reported as:

$$[(0.5*100\%)+(1.082*98.75\%)+(0.902*96.25\%)]\div 3=0.812$$
inches relative to the initial starting point.

Stated differently, this value is the estimated actual starting point for the current compression.

Mathematically, the reported value of the current starting point is expressed as:

$$Ds=\{\Sigma[DB_{i\text{-}j}+(DB_{i\text{-}j}-DB_{i\text{-}j})*P_s]*\omega^{i-1}\}\div n_r$$

where $DB_i=0$ if $DB_i>B$, where Ds is the depth of the current starting point, $n_r$ is the number of starting points remaining after all starting points that exceed the baseline have been disregarded, i is the starting point number, DBi is the measured depth of the $i^{th}$ starting point, j is the index for the most recent starting point that was still within the baseline, $DB_{i\text{-}j}$ is the most recent starting point that was still within baseline, $P_s$ is the probability that a step of size $DB_i-DB_{i\text{-}j}$ will occur, ω is the weighting constant, and B is the baseline. The result, Ds, is the reported depth of the current starting point. Expressed differently, $[DB_{i\text{-}j}+(DB_i-DB_{i\text{-}j})*P_s]*\omega^{i-1}$ is summed from i=1 to n and the sum is divided by $n_r$, but if a particular $DB_i$ is greater than B (the baseline) then that $DB_i$ is instead set to zero.

In another embodiment, a probability is assigned to the step size between the depth of the current starting point and the weighted average of all previous starting points. (In the above example, the probability is assigned to a step size between the current starting point and the immediate past starting point). This technique may be referred to as a "weighted moving average with memory" technique. In this technique the reported depth of the current starting point is expressed mathematically as:

$$Ds=\{\Sigma[DB_{i\text{-}j}+(DB_i-Ds_{i\text{-}j})*P_s]*\omega^{i-1}\}\div n_r$$

where $Ds_{i\text{-}j}=[\Sigma(DB_{i\text{-}j}*\omega^{i-2})]\div n_r$ and $DB_i=0$ if $DB_i>B$, where the variables are defined above. Again, the value for Ds is also the estimated actual starting point for the current compression.

In another embodiment, an autoregressive moving average (ARMA) filter may be used as the baseline limiter. The ARMA filter is an exponentially decaying "forgetting" filter that weights more current data more heavily than past data. The ARMA operates on more than just the compression starting point or peak values. Instead, the ARMA filter operates on data samples of compression acceleration, velocity, or depth taken at rapid time intervals. Data samples may be taken at a rate of about 100 samples per second to about 2000 samples per second (with a rate of about 1000 samples per second preferred). Thus, the ARMA filter operates on the entire waveform and not just on the compression peaks and the starting points.

In low pass form (which eliminates high frequency variations in the baseline) the ARMA filter may be expressed mathematically as:

$$y[n]=(1-\alpha)*y[n-1]+\alpha*x[n].$$

In this case, n is the index of the current sample (the "$n^{th}$" sample), y[n] is the output of the current sample, x[n] is the input of the current sample, y[n−1] is the output from the previous sample, and α is an independent term that determines how fast the filter "forgets" past outputs and the amount of influence the current input has on the output. The value for α may be in the range of about 0.02 to about 0.0002, with a value of about 0.002 being suitable for many CPR-related filter applications. Should it be desired to implement a high-pass ARMA filter for the baseline limiter, then the ARMA equation becomes:

$$y[n](\text{high pass})=1-\{(1-\alpha)*y[n-1]+\alpha*x[n]\},$$

where y[n](high pass) is the high pass filter output and the other variables are defined in the context of the low pass ARMA filter. The high pass filter may be used to eliminate low-frequency variations in the depth, velocity, or acceleration signals.

The moving average techniques in the above examples have been described in the context of processing the compression depth waveform. However, the techniques can be used to process the velocity waveform and the acceleration waveform, should it be desired to report accurate values for the velocity and acceleration of compressions. The moving average techniques may be applied to each waveform separately. In other words, one does not necessarily apply a moving average technique to the acceleration waveform, then integrate the acceleration waveform, then apply a second moving average technique to the velocity waveform, then integrate the velocity waveform, and finally apply a third moving average technique to the depth waveform. However, in other embodiments this procedure may be used.

Other methods for analyzing the baseline signal may be used to determine the estimated actual starting point of compressions. Another embodiment of the baseline limiter comprises a signal processor that uses a transition probability map to identify the probability of particular shifts in the measured starting point. (The probability map may be predetermined, such as by using a density estimator or kernel estimator, and then hard-coded into the compression monitor software.) A particular starting point measurement is compared to the probability map and the system determines by how much a given shift in the measured starting point is erroneous. The reported starting point is adjusted accordingly. (Likewise, a transition probability map may be used to estimate the actual peak and also the actual maximum depth for each compression.)

Figure 13:
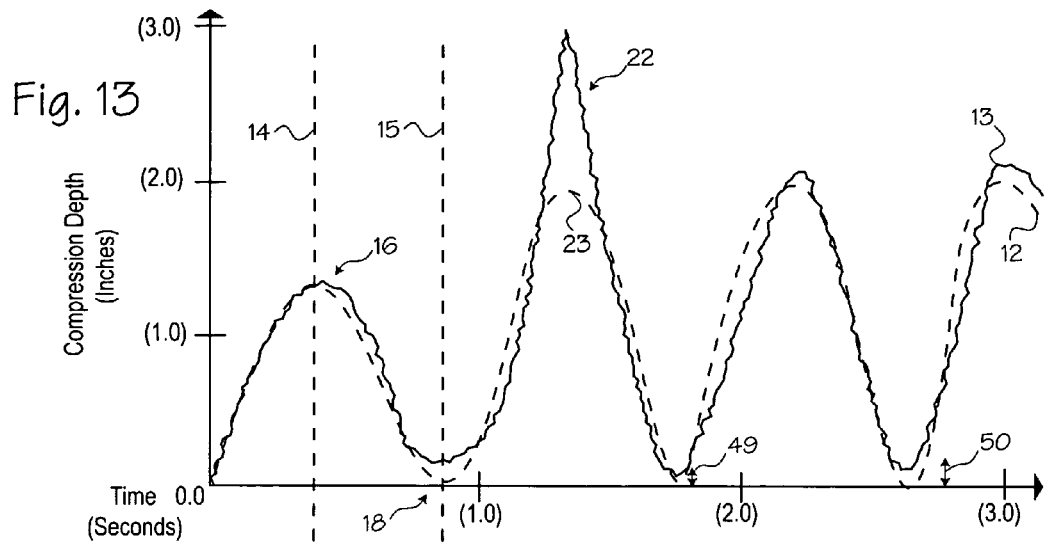
FIG. 13 shows the graph of compression depth over time after filtering both the raw acceleration and the derived velocity, and after applying a baseline limiter to the compression depth waveform.
Figure 14:
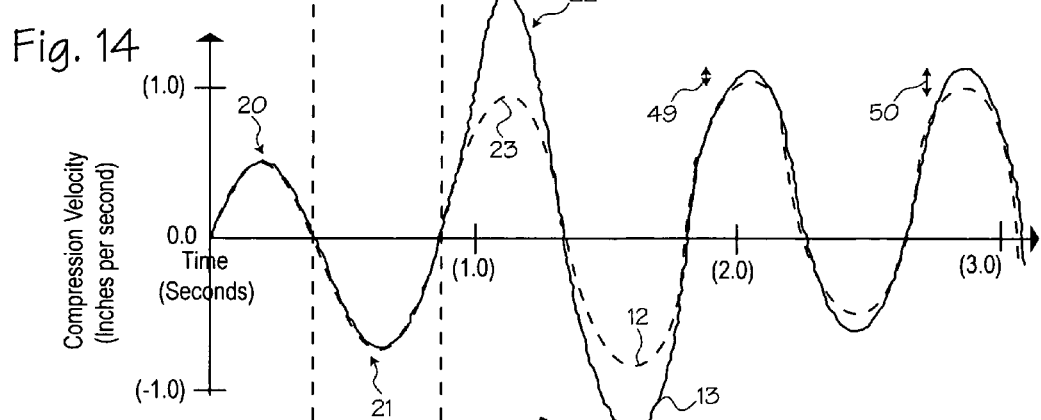
FIG. 14 shows the graph of compression velocity over time after filtering both the raw acceleration and the derived velocity, and after applying the baseline limiter to the compression velocity waveform.
Figure 15:
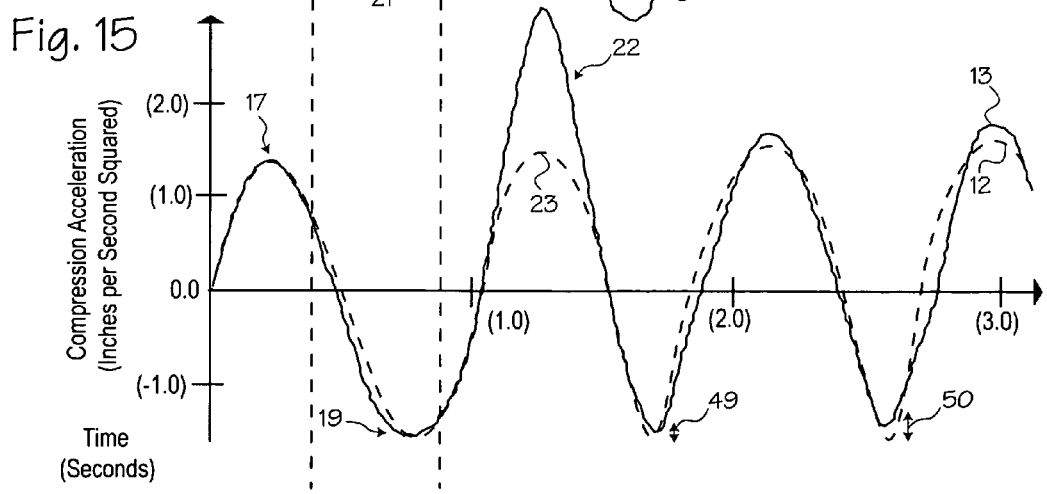
FIG. 15 shows the graph of compression acceleration over time after filtering the raw acceleration and after applying the baseline limiter to the compression acceleration waveform.

The effect of the baseline limiter 39 is seen in FIGS. 13 through 15, which show the graphs of compression depth, velocity, and acceleration over time for four hypothetical compressions. FIGS. 13 through 15 also show the output of steps 35 through 39 in FIG. 5. The baseline limiter has been applied separately to the velocity waveform (FIG. 14) in step 47 and to the acceleration waveform (FIG. 15) in step 48.

FIGS. 13 through 15 show that a moving average technique reduces the effect of drift in the reported starting point of each compression. (The moving average techniques also reduce the effect of external acceleration errors that appear in the baseline portion of the waveform). Before correction, the reported starting points were becoming increasingly deeper, though the actual starting points were returning to close to the actual initial starting point. By applying a moving average technique to the baseline of a measured waveform, the reported starting points of each compression are statistically closer to the actual starting points. Accordingly, the compression monitor will report an estimated actual compression depth that is closer to the actual compression depth. Arrows 49 and 50, which are shorter than arrows 24 and 25 in FIGS. 2 through 4 and FIGS. 7 through 12, show the beneficial effect of applying a moving average technique to each waveform.

Returning to FIG. 5, the compression depth waveform corrected by the baseline limiter may be passed through a third filter in step 51 to reduce any accumulated signal noise in the compression depth waveform. The third filter comprises a high pass filter, though in other embodiments the third filter may comprise a band pass filter.

Subsequently, the depth waveform (whether filtered or unfiltered) is provided to a starting point detector in step 52. The starting point detector identifies the value of the current estimated starting point. The current estimated starting point is then provided to a means for combining signals 53 (as indicated by line 54). The means for combining signals 53 will later use the current estimated starting point to calculate the estimated actual compression depth. The means for combining signals comprises a signal adder, a linear system model, a non-linear system model, or other means for combining signals.

Next, the compression waveform may be provided to a peak limiter in step 55. The peak limiter is a signal processor that performs similar functions to the baseline limiter, but instead operates on the peak portion of a compression waveform. The peak portion of the waveform comprises that portion of the waveform in which a peak is most likely to occur. In one embodiment, the peak portion is the portion of the waveform above the baseline portion. Continuing the example given for the baseline limiter, the peak portion of the depth waveform would be the portion of the depth waveform that is above 1.1 inches. The peak limiter thus will smooth the peak portion of a waveform in much the same way as the baseline limiter smoothes the baseline portion of a waveform.

In one embodiment the peak limiter sets an outside boundary on the size of the maximum compression depth. Thus, the peak limiter either disregards (throws out) or sets an arbitrary value to any peak that is greater than a known, improbable peak value (the depth of a large person's chest, for example, would not be a probable value for CPR compression depth). Thus, the peak limiter prevents the compression monitor from reporting a compression depth that is improbable.

The effect of the peak limiter is seen in FIGS. 16 through 18, which show the graphs of compression depth, velocity, and acceleration over time for four hypothetical compressions after the peak limiter step 55 in FIG. 5. (FIGS. 16 through 18 show the output of steps 35 through 55). A peak limiter has been applied separately to the velocity waveform in step 56 and to the acceleration waveform in step 57. By applying a moving average technique to the peak portion of the compression waveforms, the effect of the external acceleration spike 22 has been greatly reduced. Combined with the techniques discussed in the previous processing steps, the reported waveforms are now close to the actual waveforms.

Returning to FIG. 5, the estimated peak may optionally be provided to a fourth filter 58 to remove remaining signal noise. The fourth filter comprises a high pass filter, though in other embodiments the fourth filter may comprise a band pass or other filter.

Subsequently, the depth waveform is provided to a peak detector in step 59. The peak detector identifies the value of the estimated peak (the estimated maximum depth of the current compression). The estimated peak is then provided to the means for combining signals 53. The means for combining signals 53 combines the estimated starting point 52 with the estimated peak 59 to produce an estimated actual compression depth for the current compression 61. The estimated actual depth is then provided to a means for user feedback 62 (a user feedback system). The means for user feedback may comprise a speaker, a visual display, one or more LEDs, a vibrator, radio, or other means for communicating with the rescuer. The user feedback system in turn provides information corresponding to the estimated actual depth of the current compression to the rescuer.

In the technique of FIG. 5, the baseline portion and the peak portion do not overlap. Thus, the compression depth waveform may be thought of as comprising two portions, the baseline portion and the peak portion. Each portion of the depth waveform is treated differently by two different procedures (the baseline limiter and the peak limiter) to extract different information. Thus, both the baseline limiter and the peak limiter operate on the same depth waveform. The effect of this is that the signal comprising the depth waveform is provided first to the baseline limiter and then to the peak limiter (the signal is not split).

The technique shown in FIG. 6 may be used when the baseline portion and the peak portion overlap (though the technique may also be used when the baseline portion and peak portion do not overlap). For example, the technique of FIG. 6 may be used when the baseline portion is set below 1.5 inches (relative to the chest's relaxed position) and the peak portion is set above 1.0 inches (relative to the chest's relaxed position). In this case the signal representing the depth waveform is split and is provided to two separate processors, a baseline limiter and a peak limiter. Each processor performs similar functions to the limiters already described. Thus, although the baseline limiter and the peak limiter act independently of each other, the technique of FIG. 6 produces an estimated starting point and an estimated peak in much the same was as the technique shown in FIG. 5. The means for combining signals then combines the estimated starting point and estimated peak in step 53 to produce the estimated actual depth of the current compression. The estimated actual depth of the current compression is provided to the user feedback system in step 62. The user feedback system in turn provides the estimated actual depth of the current compression to the rescuer.

Figure 19:
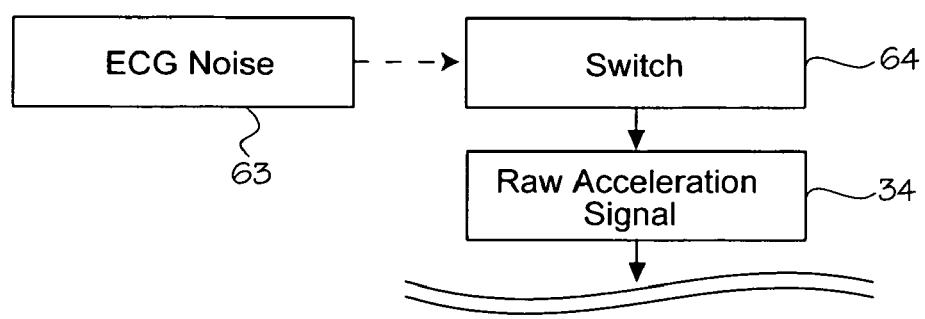
FIG. 19 is a flow chart of a signal processing technique that uses a change in ECG noise to activate a switch which, in turn, controls when an accelerometer begins to measure acceleration.

In addition to the signal processing techniques of FIGS. 5 and 6, other techniques can be used to correct for errors in the compression depth waveform. For example, FIG. 19 is a flow chart of a signal processing technique that uses a change in ECG noise 63 to activate a switch 64 that, in turn, controls when an accelerometer begins to measure acceleration.

To implement this technique, the compression monitor is provided with one or more electrodes, or some other means for measuring the patient's ECG. As the rescuer performs compressions the patient's ECG becomes noisy. Even if the patient's actual ECG is flat (shows no activity) the reported ECG will still show the noise caused by chest compressions. Indeed, a motion artifact signal (an ECG noise component caused by chest compressions) will be superimposed on any ECG rhythm. Whatever the actual ECG rhythm, the ECG noise may be isolated and accounted for.

Since the bulk of ECG noise during compressions is caused by the act of compressing the chest, the starting point of a compression may be correlated to the point where the ECG noise exceeds a pre-determined threshold. However, there is some delay or lag between the onset of a compression and the onset of ECG noise. The time lag is on the order of milliseconds to tenths of a second. In order not to miss any part of a compression, a buffer (either digital or analog) may be employed to correct for the time lag. Thereafter, when the ECG noise exceeds the particular threshold then the switch is programmed to activate the accelerometer (which will begin to take acceleration measurements). Total compression depth is then determined by double integrating the measured acceleration.

The effect of using ECG noise as a reference sensor to establish the starting points of compressions is seen in FIGS. 20 through 25, which show compression depth, velocity, and acceleration over time for four hypothetical compressions. No signal processing is applied to any of waveforms shown in FIGS. 20 through 22. The phantom waveforms 12 represent the actual waveforms for compression depth, velocity, and acceleration (measured independently of the accelerometer). The solid waveforms 13 represent the waveforms derived from the acceleration measured by the accelerometer. The solid waveforms are also the waveforms reported by the compression monitor. The effects of signal noise are shown by the rough nature of the solid waveforms. The effects of external acceleration noise are shown by the two spikes, 65 and 66, in the reported waveform. The effects of negative drift (increasingly shallow compressions) are shown by the increasing distance (represented by arrows 67 and 68) between the minimums in the reported and the actual waveforms.

The effect of using ECG noise as a reference sensor to establish the starting points of compressions is seen in FIGS. 23 through 25, which show graphs of compression depth, velocity, and acceleration over time for hypothetical compressions. Using ECG noise as a reference sensor reduces certain external acceleration errors and reduces the effect of negative drift. (The ECG noise reference sensor can also reduce the effect of positive drift). Specifically, the ECG noise reference sensor reduces the effect of external acceleration noise that occurs near a compression minimum. Since the accelerometer is not "on," a portion of the external acceleration spike is "ignored". In practice the accelerometer is still taking data, but software or hardware is used to process out accelerometer data or signals that occur during a time period where ECG noise does not reach a predetermined level. In other methods, the estimated actual depth of compressions is calculated when the ECG noise falls within a predetermined threshold. In any case, the effect of spike 65 is reduced in the reported waveform. However, the accelerometer by itself still cannot tell the difference between a compression-related acceleration and an external acceleration. Thus, the reported waveform is still subject to external acceleration noise that occurs during a compression, as shown by spike 66.

Nevertheless, the ECG noise reference sensor does reduce the effects of drift. Since the starting point of a compression is independently established, the waveform is much less subject to either positive or negative drift. In other words, the accelerometer will always measure acceleration after the actual start of compressions. Thus, the reported waveform of FIG. 23 more accurately shows what the rescuer is actually doing—compressing the chest from starting points that are becoming increasingly deep. Thus, peaks 69 and 70 show that the measured waveform more closely matches the actual waveform.

Although the ECG noise reference sensor can reduce the effects of drift and reduce the effect of some forms of external acceleration noise, signal noise remains a problem. Thus, FIGS. 23 through 25 still show the same levels of signal noise as shown in FIGS. 20 through 22. To reduce all forms of noise the ECG noise reference sensor may be combined with the signal processing techniques of FIGS. 5 or 6. The combined techniques will produce a reported depth waveform that is close to the actual waveform.

Figure 26:
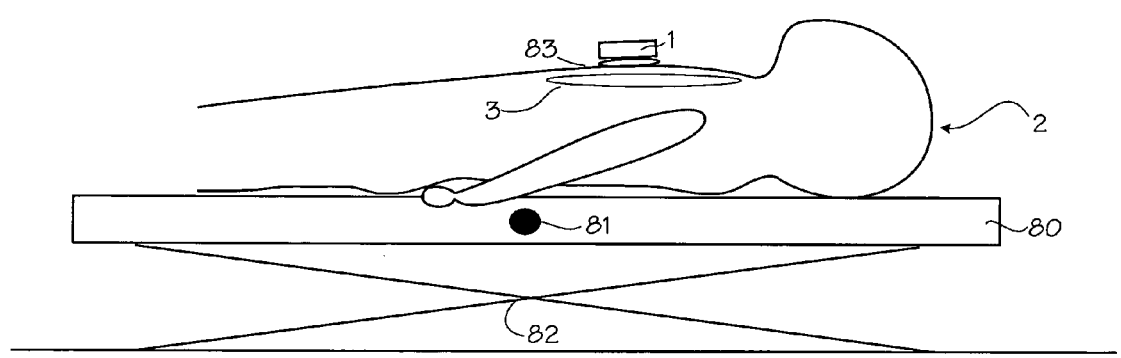
FIG. 26 shows an accelerometer-based compression monitor in place on a patient and a system of reference sensors comprising a reference accelerometer, a switch, and a load sensor disposed such that each sensor may measure various parameters related to chest compressions.

Other reference sensors may be used to establish the actual starting point of a compression. FIG. 26 shows an accelerometer-based compression monitor in place on a patient 1 who is lying on a surface 80. A system of reference sensors comprising an accelerometer 81, a load sensor 82, and a switch 83 are disposed such that each sensor may measure various parameters related to chest compressions. In the case of reference accelerometers, the reference accelerometers may be disposed elsewhere on the patient, or upon any reference object that experiences the same external accelerations the patient experiences. The reference accelerometers may comprise a three-axis accelerometer, but may also comprise three orthogonal single-axis accelerometers or one single axis accelerometer (in which case the accelerations along the other two axes are assumed to be negligible).

The reference accelerometers 81 allow a signal processor to eliminate external acceleration error, such as those accelerations caused by transporting the patient. In one method, the acceleration sensed by the compression monitor or automatic CPR device (the device acceleration) is provided to a signal processor. The device acceleration contains the acceleration caused by compressions (the compression acceleration) and the acceleration caused by the external accelerations (the external acceleration). Next, the reference accelerometer or accelerometers provide a reference acceleration to the signal processor. The reference acceleration contains only the external acceleration of the patient. Then the reference acceleration is combined with the device acceleration to produce an estimated actual acceleration. (The effect of compression accelerations on the reference acceleration is negligible since the surface and patient are kept steady with respect to the compression monitor.)

Once obtained, the estimated actual acceleration may be double integrated to produce an estimated actual chest depth. Thus, the depth of compressions may be determined even in the presence of large external accelerations. Moreover, the position signal may be made more accurate and precise by combining the actual acceleration with the signal processing technique of FIG. 5 or 6, or with other signal processing techniques.

In lieu of (or in addition to) the ECG noise sensor and reference accelerometers, other reference sensors may be used to set the actual starting point of a compression. Reference sensors may comprise a load sensor 82, a switch 83, a transthoracic impedance detector, an ECG noise detector (as described above), a voltage or current sensor in an automatic CPR device, a start signal in an automatic CPR device, an encoder in an automatic CPR device, or any other sensor capable of independently detecting the actual beginning of a compression. When the reference sensor detects the beginning of a compression then the starting point is set to zero. The acceleration is then processed to derive compression depth. The technique of setting the starting point to zero when a reference sensor detects the beginning of a compression may also be combined with the signal processing techniques of FIGS. 5 or 6.

In the case of a switch 83, the switch is disposed such that when a compression begins the switch will be closed. For example, the switch may be disposed beneath or on the compression monitor, on the patient 1, on the surface 80 upon which the patient lies, on the rescuer's hand, on a CPR machine, on the patient, or on some other location that allows the switch to register that a compression has begun.

The switch may comprise many different types of switches and sensors, including a contact switch, a motion sensor, a voltage sensor on an automatic CPR device, an optical, rotary, or other encoder on an automatic CPR device, the displacement of a shaft or other component on an automatic CPR device, a potentiometer, a strain gage, a piezoresistive transducer, a differential transformer, synchro and induction potentiometers, variable-inductance and variable-reluctance pickups, an eddy current non-conducting transducer, a capacitive transducer, an electro-optical transducer, a photographic switch, a video tape switch, a holographic switch, a switch that uses photoelastic techniques, translation encoders, an ultrasonic transducer, moving coil and moving magnet pickups, an AC or DC tachometer, an eddy-current drag-cup tachometer, additional accelerometers, or a gyroscopic displacement switch.

In the case of the load sensor 82, the load sensor may be operatively connected to the rescuer, the patient, an automatic CPR device, beneath the patient, or elsewhere so long as the load sensor senses a load when compressions begin. When the load sensor measures a load that exceeds a pre-determined threshold, then the measured starting point is set to zero. The load sensor may also be operatively connected to a switch, which activates when the load sensor senses a load, or the load sensor may merely provide input to a signal processor system identifier (described in more detail below). Compression depth is then determined by integrating the acceleration twice. The technique of setting the starting point to zero when a load sensor detects the beginning of a compression may also be combined with the signal processing techniques of FIG. 5 or 6.

In another embodiment of the load sensor 82, the load sensor may be disposed such that the sensor can sense both the weight of the patient and the force of compressions. The load sensor 82 may be disposed beneath the surface 80 upon which the patient 1 rests. During compressions the force of pressing on the patient causes the load sensor to report a total force greater than the patient's weight. Accordingly, a starting point is set to zero when the total force is about equal to the patient's weight.

Examples of force sensors that can be used with this technique include pressure sensors, elastic force transducers, shaft displacement on an automatic CPR device, a voltage or a current sensor on an automatic CPR device, an optical, rotary, or other encoder on an automatic CPR device, bonded strain gages, beam strain gages, differential transformers, piezoelectric transducers, variable reluctance/FM oscillators, gyroscopic force transducers, and vibrating wire force detectors. Examples of pressure sensors that can be used with this technique include deadweight gages, manometers, elastic transducers, piezoelectric transducers, and force-balance transducers.

In the case of a transthoracic impedance detector, one or more ECG, defibrillation, or other electrodes are disposed on the patient's thorax. When a compression begins the impedance of the thorax changes. The thoracic impedance comprises the impedance due to skin and thoracic contents between any two electrodes. The change in thoracic impedance may be measured by a small test current or by any other means for measuring impedance. When the impedance changes by a pre-determined amount then the starting point is set to zero. Total compression depth may then be determined by processing the measured acceleration.

Figure 27:
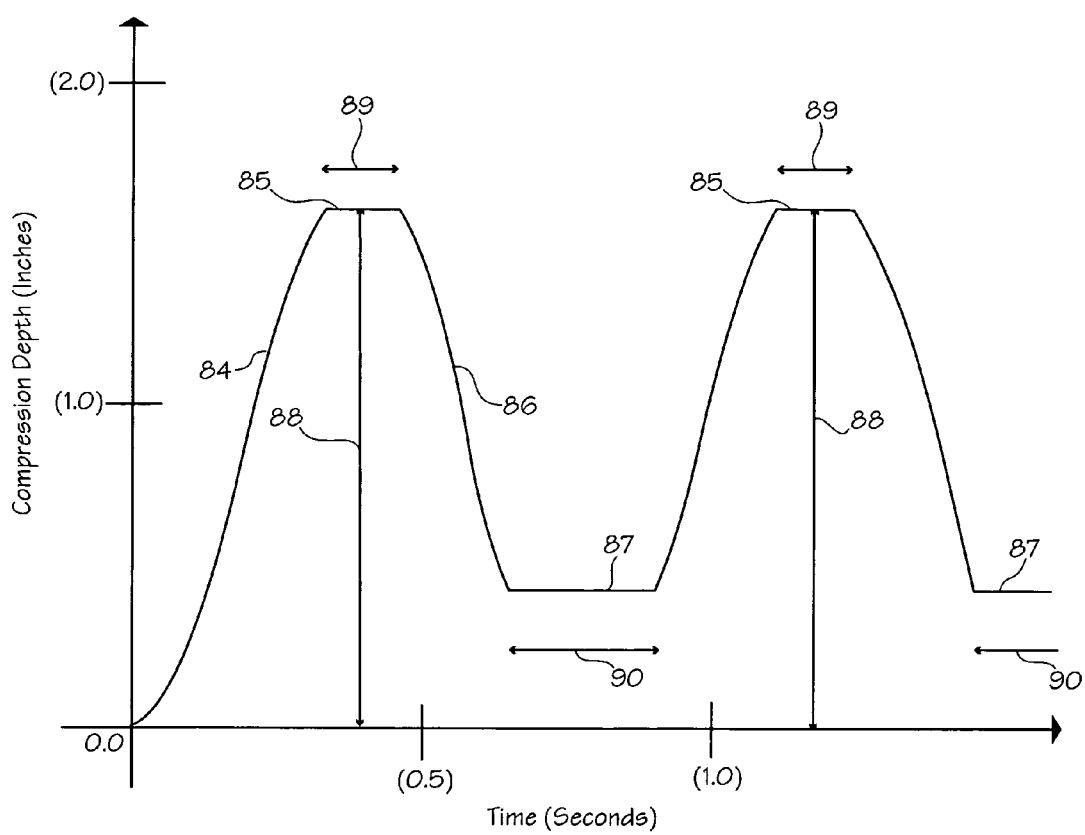
FIG. 27 illustrates a compression waveform that a user feedback system may prompt the rescuer to perform.

Because the compression monitor can measure the compression waveform, the compression monitor can also prompt the rescuer or an automatic CPR device to perform a particular compression waveform. FIG. 27 shows a compression waveform that the compression monitor may prompt the rescuer to perform. Depth is measured in inches and time is measured in seconds. The scale shown in FIG. 27 is marked in 0.5 second intervals and 1.0 inch intervals respectively. The compression phase of the cycle is indicated by the positively sloped curve 84. The compression phase of the cycle ends at the maximum compression depth 85 (compression peak). The decompression phase of the cycle is indicated by the negatively sloped curve 86. The decompression phase ends when the rescuer begins a new compression at the next starting point 87 (or baseline), which may or may not be at the initial starting point. Compressions are initiated at time=0 and depth=0, and the total depth of compressions is the distance represented by arrows 88.

The compression waveform includes a compression hold 89, where the rescuer maintains a hold at maximum compression depth for a short period of time, and an incomplete decompression hold 90, where the rescuer maintains a short hold at a point deeper than the initial starting point. Each compression and decompression is performed quickly, at high acceleration and velocity, as indicated by the relatively steep slopes of the compression phase 84 and the decompression phase 86. The duty cycle is slightly less than 50% (the ratio of compression and decompression time is 1), meaning that slightly less time is spent in the compression phase, as indicated by the distance between arrows 89, than in the decompression phase, as indicated by the distance between arrows 90.

Although the compression waveform of FIG. 27 shows an example of a particular waveform that the compression monitor can instruct a rescuer to perform, other waveforms are also possible. For example, another waveform may lack a compression hold phase. Yet another varies the duty cycle and others increase the compression hold time. The exact waveform depends on the current state of the art of what kind of compression waveform comprises an optimal compression waveform for a particular kind of patient. In addition, the compression monitor may be provided with a switch, button, software, or other means for user input which allows the rescuer to enter the size or shape of the patient. The compression monitor may use this information to choose a particular waveform from a library of waveforms. The compression waveforms are thus adaptable to findings in future research, AHA guidelines, rescuer observations, and medical professional preferences. Accordingly, at various times different waveforms may be provided to the user feedback system, as described more fully below.

The prompted waveform may be provided by the user feedback system (step 62 in FIG. 5). In addition, the user feedback system may provide the rescuer or automatic CPR device with other compression-related information. For example, the user feedback system may display information regarding the starting point of compressions, the compression depth waveform, the compression velocity waveform, and the compression acceleration waveform. Thus, the user feedback system may provide the rescuer or the automatic CPR device with all of the data needed to continuously track the position, velocity, and acceleration of the chest during all phases of CPR. This information may be used to evaluate the performance of a rescuer or automatic CPR device.

The user feedback system may also provide a rescuer or automatic CPR device with information concerning the compression phase quality and the decompression phase quality. Compression phase quality is the quality of compressions with respect to total compression depth, the duty cycle, the acceleration of compressions, smoothness of compressions, and other factors related to the compression phase. Decompression phase quality is the quality of compressions with respect to whether the rescuer returns to the actual initial position, the duty cycle, the acceleration of decompressions, the smoothness of decompressions, and other factors related to the decompression phase. The rescuer or automatic CPR device may use this information to evaluate or prompt the kind and quality of compressions.

The user feedback system 62 may provide the rescuer or automatic CPR device with information concerning compression phase quality by combining information gained from the acceleration, velocity, and position waveforms. For example, the user feedback system can instruct the rescuer to increase compression force when the depth of compressions are less than recommended guidelines and to reduce compression force when the depth of compressions are greater than recommended guidelines. The user feedback system may also instruct the rescuer with regard to other compression phase parameters of a compression waveform. For example, the user feedback system can inform the rescuer or automatic CPR device if the time to achieve proper compression depth is too short or too long.

The user feedback system 62 may also provide the rescuer or automatic CPR device with information regarding decompression phase quality by combining information gained from the acceleration, velocity, and position waveforms. For example, the user feedback system can instruct the user or device on the proper position at which to rest after a decompression. Thus, the feedback system can instruct the user or device to allow the chest to fully relax if the rescuer or device is not allowing the chest to fully return to its initial starting position. Conversely, should it be medically indicated, the user feedback system can instruct the user or the device to return to a depth just below the initial chest position. In this case, the rescuer or device implements a "decompression hold" and maintains force on the chest even when the compression cycle reaches its minimum depth. In another case the feedback system can indicate different compression starting points at different times. Thus, the user feedback system can instruct the rescuer or device to apply incomplete decompression holds during compression cycles, but to allow the chest to return to its fully relaxed position during ventilation pauses. The user feedback system may also instruct the rescuer or device with regard to other decompression phase parameters, such as the decompression rate and the duty cycle of the decompression phase.

Taken together, the information gained from the compression phase quality and the decompression phase quality enable the user feedback system to prompt the rescuer on how to perform an optimum compression waveform and an optimum compression duty cycle. A rescuer performs a particular compression waveform by performing compressions at a pre-determined depth and rate, and by holding the chest at a pre-determined compression depth for a pre-determined time. A rescuer performs a particular duty cycle by compressing the chest for a pre-determined period and allowing the chest to relax for another pre-determined period.

Thus, the user feedback system can prompt the rescuer or automatic CPR device to perform at the appropriate compression rate, compression depth, compression velocity (the time required to compress or decompress the patient), compression acceleration, and compression hold time for each phase (compression and decompression) of the compression cycle. Accordingly, the compression waveform that the rescuer or device actually applies can conform to a complex compression waveform. Since research has shown that most patients benefit from more complex waveforms, patient survival is likely to increase if the rescuer or automatic CPR device uses a compression monitor with this user feedback system.

Similarly, the user feedback system 62 of FIG. 5 can provide the rescuer or CPR device with feedback regarding the compression duty cycle. The duty cycle is the ratio of time under compression to the time under decompression for each compression cycle. (However, the duty cycle does not include time periods where no compressions are taking place, such as during ventilation.) If the duty cycle does not fall within pre-determined parameters, then the user feedback system may prompt the rescuer to adjust compression timing and compression rate in order to effect an optimal duty cycle.

The user feedback system described above comprises the last step in a particular solution to the problem of determining an accurate value for chest displacement from a raw acceleration signal. (FIG. 5 is the flowchart for this solution). Many variations of that solution exist, as already described, though it is possible to view the problem from a general perspective and to create a general solution.

Figure 28:
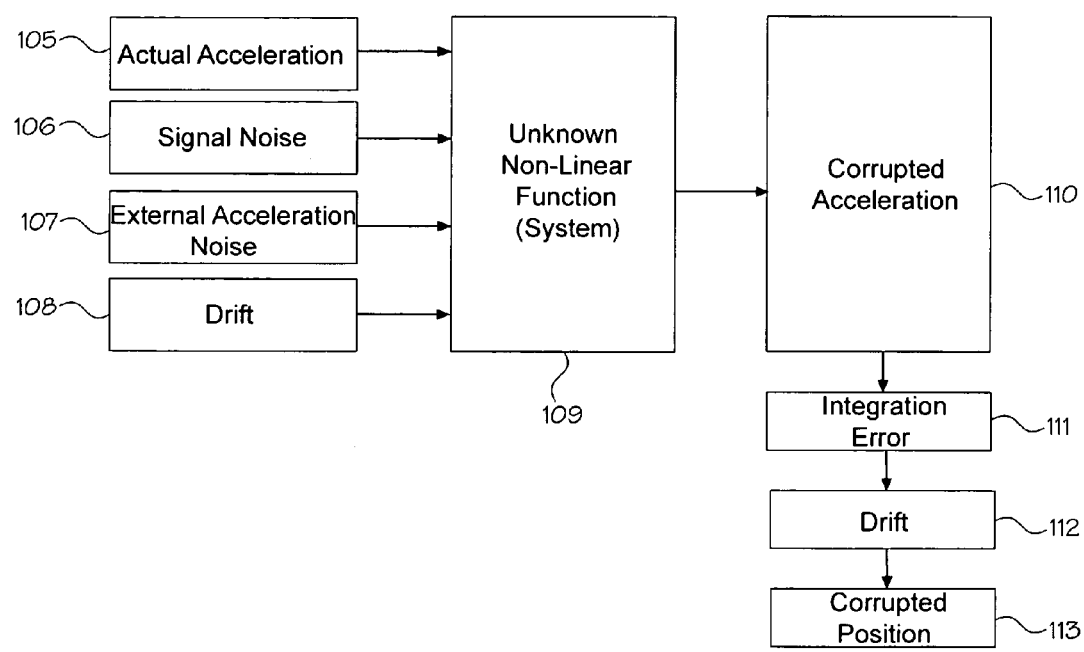
FIG. 28 is a block diagram of how an actual chest compression acceleration is converted into a corrupted value for chest position.
Figure 29:
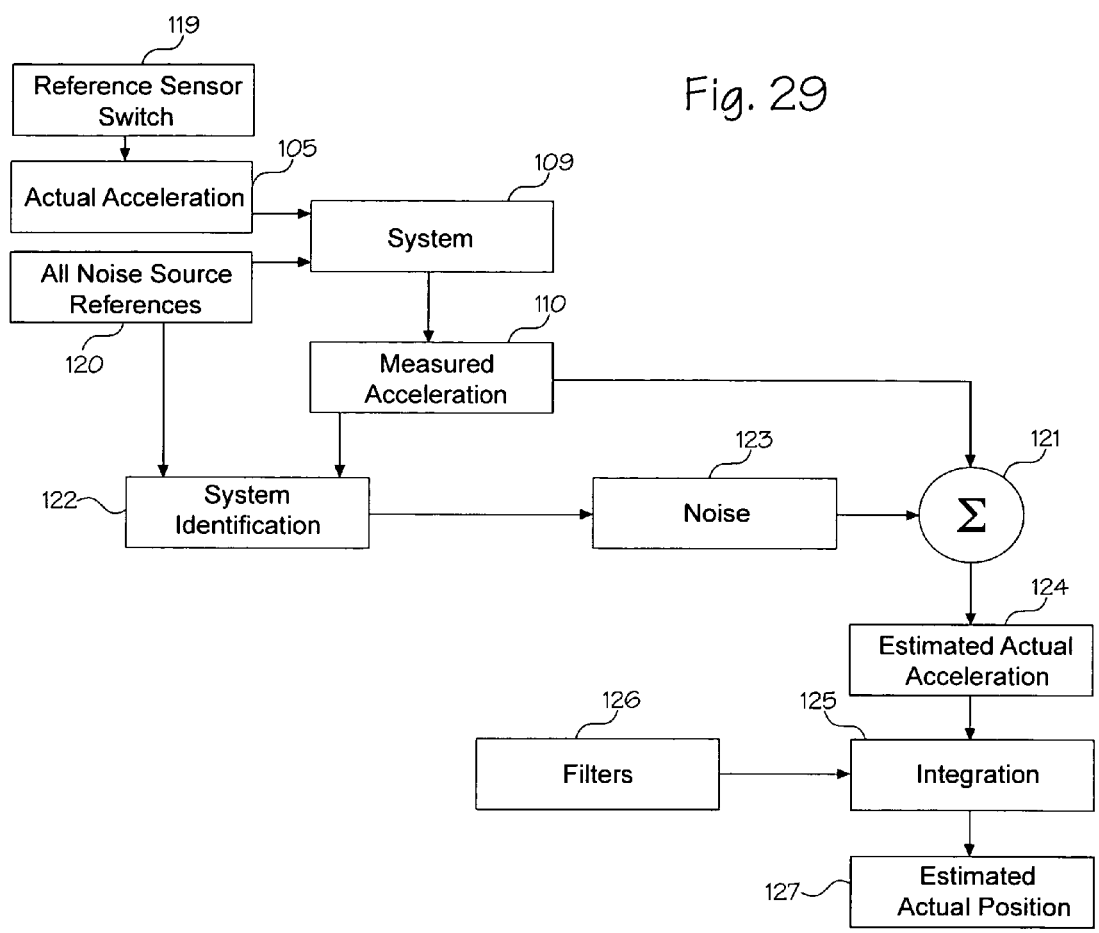
FIG. 29 is a block diagram of a general solution for converting a corrupted chest compression acceleration into an estimated actual depth of chest compressions.

FIGS. 28 and 29 are block diagrams that represent the general problem to and the general solution for determining an accurate position from an acceleration measured during CPR. FIG. 28 is a block diagram of how an actual chest compression acceleration is converted into a corrupted value for chest position. In broad terms, the actual acceleration 105, signal noise 106, external acceleration noise 107, and some forms of drift 108 are combined by an unknown function 109 (which may be linear or non-linear and may include random or deterministic inputs). The unknown non-linear function is known as the system, which produces the corrupted acceleration 110 measured by the accelerometer. The corrupted acceleration is then integrated twice, which greatly compounds the problem introduced by the corruption in the acceleration. The increased error is referred to as integration error 111 (although it is assumed that the integration technique itself does not directly contribute errors into the position). Finally, additional sources of drift 112 can affect the final value for the corrupted position 113.

FIG. 29 is a block diagram of a general solution for converting a corrupted chest compression acceleration into an estimated actual depth of chest compressions. First, a reference sensor 119 may establish the actual starting point of a compression. Thus, the starting point of the acceleration will be known. (Although helpful, the reference sensor 119 is not necessary to the general solution). The actual acceleration 105 and the real or the estimated noise sources 120 (which comprise blocks 106 through 108 of FIG. 28) are combined by the system 109 by an unknown function. The result is the corrupted acceleration 110. The measured acceleration is then provided to a means for combining data 121 (which may comprise a linear or a non-linear function) and to a system identifier 122.

The system identifier comprises one or more functions (either linear or non-linear) that model the system. One or more noise references that can be correlated to the noise sources 120 may also be provided to the system identification function 122. For example, noise identified by a low frequency filter can be correlated to signal noise or a reference accelerometer can be correlated to the external acceleration noise.

The system identification function may also use various parameters of an automatic CPR device as noise source references, even if the reference itself does not produce noise in the acceleration. However, the noise source reference must somehow be correlated to a source of noise in the acceleration signal. For example, the accelerometer-based depth measurement reports a chest depth of 0.5 inches. However, a simultaneous current spike in the automatic CPR device informs the system that the CPR device is compressing the chest much harder than should be required to achieve a chest depth of 0.5 inches. The discrepancy may be caused by external acceleration noise or by drift. Thus, the current spike may be correlated to a source of noise in the system. This information may be used by the system identifier to help model the system. Likewise, voltage, shaft displacement, or optical or rotary encoders may be used as references by the system identifier to help model the system. (Again, the noise references are useful but not necessary).

The system identifier then combines or correlates the noise source references and the measured acceleration in order to produce the estimated noise 123 in the measured acceleration. The estimated noise 123 is then provided to the means for combining data 121. The means for combining data combines the estimated noise 123 and the measured acceleration 110 to produce an estimated actual acceleration 124. The estimated actual acceleration is then integrated 125 twice. Filters 126 may optionally be used during one or both integration steps to reduce the compounding effect of errors that may still linger in the estimated actual acceleration. The final result is an accurate and precise estimate of the actual position 127 of the accelerometer.

The system identification function 122 models the system and thus can be used to estimate the noise in the acceleration. (Once the noise is known it can be easily eliminated by combining the noisy acceleration with the measured acceleration.) In other words, system identification is the process of using the input and output data to model the function that combines the actual acceleration and the sources of noise in the acceleration. The system identification problem has a known or measured output and an input that may be known or unknown. The addition of known or measured input is beneficial to system identification, but not necessary. The system itself is an unknown arbitrary function that can be linear or non-linear, though some boundary conditions may be known.

A number of methods, both linear and non-linear, may be used to model the system. Each of these methods may comprise, alone or in combination, the system identification function in step 122. These methods may operate by taking many data samples per second, as opposed to operating only on the compression starting points or peak points. Nevertheless, these methods may also be performed on the compression starting points or the compression peaks. A partial list of these methods include: autoregression, autoregression with extra inputs, autoregressive moving average (which is one of the methods used in the techniques shown in FIGS. 5 and 6) autoregressive moving average with extra inputs, autoregressive integrated moving average, autoregressive integrated moving average with extra inputs, a Box-Jenkins model, an output error model, a hidden Markov model, a Fourier transform, a wavelet transform, wavelet de-noising, wavelet filtering, adaptive neural networks, recurrent neural networks, radial basis function nets, adaptive curve fitting (splines), Kalman filters, extended Kalman filters, adaptive Kalman filters, unscented Kalman filters, and kernel estimation. Algorithmic approaches that may be used to find the system identification function include maximum entropy, maximum likelihood, recursive least squares (or similar techniques), numerical methods, unconstrained global search or optimization, expectation minimization, and fast Fourier transforms.

In the case of recursive identification, the formula for general recursive identification may be expressed as:

$$X(t) = H(t, X(t-1), y(t), u(t)) \text{ and} \quad (1)$$

$$\theta(t) = h(X(t)), \quad (2)$$

where X(t) is the state of the system at time t; H is the state of the transfer function; X(t−1) is the past system state; Y(t) is the measured output; u(t) is the measured input; θ(t) is the system, and h transforms the system state to the output. The system state can be converted to the system output by h(X(t)).

Since X(t) and θ(t) are evaluated at each time point as u(t) and y(t) are collected, the total amount of previously collected data has a much more profound effect on the system than do the most recently collected data.

Equations (1) and (2) may be simplified into equations (3) and (4):

$$X(t) = X(t-1) + \mu Q_x(X(t-1), y(t), u(t)) \text{ and} \quad (3)$$

$$\theta(t) = \theta(t-1) + \gamma Q_\theta(X(t-1), y(t), u(t)), \quad (4)$$

where μ and γ are small numbers that reflect the relative amount of information provided by the latest time step. Q is a function that relates inputs, outputs, and states. Equations (3) and (4) are more simple in the sense that it is more simple to compute the equations by recursive than equations (1) and (2).

A number of numerical algorithms may be used to solve equations (3) and (4). A partial list of numerical algorithms include recursive least squares, recursive (or recursion) instrumental variables, recursive prediction error methods, recursive pseudolinear regression, recursive Kalman filters (including time varying parameters), and recursive Kalman filters for time varying systems. These numerical techniques encompass many of the famous "named" techniques as special cases, including a Kalman filter, an extended Kalman filter, extended recursive least squares, and others. Each algorithm has strengths and weaknesses, but all asymptotically approach a solution to equations (3) and (4).

The "named" special cases may be derived from general equations (3) and (4) when certain conditions or assumptions are made. Thus, the equations for each of the listed algorithms can be further specified. For example, when using a recursive least squares algorithm equation (4) may be expressed as:

$$\theta(t) = \theta(t-1) + L(t)[y(t) - \phi^T(t)\theta(t-1)] \text{ where} \quad (5)$$

$$L(t) = \frac{P(t-1)\phi(t)}{\lambda(t) + \phi^T(t)P(t-1)\phi(t)} \text{ and} \quad (5a)$$

$$P(t) = \frac{P(t-1)}{\lambda(t)} - \frac{P(t-1)\phi(t)\phi^T(t)P(t-1)}{\lambda(t)[\lambda(t) + \phi^T(t)P(t-1)\phi(t)]}. \quad (5b)$$

In equations 5 through 5(b) L(t), P(t), and P(t−1) are terms used to simplify the equation, φ(t) is a regression vector, λ(t) is a forgetting factor (described in more detail below), and φ$^T$(t) is the transpose of the regression vector.

In addition, equation 4 can also be expressed for the cases of recursive instrumental variables, recursive prediction-error methods, recursive pseudolinear regression, a recursive Kalman filter for time-varying systems, and a recursive Kalman filter with parametric variation.

Once the system identification algorithm as been selected from the above set of algorithms, there are several additional parameters that may affect the quality of the model. These additional parameters include data weighting, choice of updating step, choice of updating gain, and model order selection. In the case of data weighting, when a system is time-varying the input-output data near the present time more accurately reflects the nature of the present system. Data recorded further back in time is more closely related to a past system state. To reflect this fact the data can be weighted to favor a more recent system state. Actual data weighting is accomplished by the "forgetting factor," λ, in equations 5 through 5b. The selection of λ is made based on information about how fast the system changes state. A typical range for λ is between about 0.9800 and about 0.9999 (though λ may be 1.0000 if no "forgetting factor" is desired).

Another way of thinking about the effect of λ on the system identifier is to evaluate at what point a data sample is given a weight of about 36%. (36% is the value of the number e$^{-1}$, which is the value at which a data sample may be considered statistically insignificant). At this weight a data sample's statistical significance becomes relatively small. The sample number at which a data sample has a weight of about 36%, known as T$_0$, may be mathematically expressed as:

$$T_0 = \frac{1}{1-\lambda}.$$

T$_0$ (and hence λ) is selected with appropriate knowledge of the system state and can be used to tune system identification so that the estimated actual acceleration most closely approximates the actual acceleration if the actual acceleration were independently measured. Thus, T$_0$ is pre-set before the compression monitor begins taking measurements.

The closer λ is to 1 the more samples are needed to reach the point where a given data sample is given a weight of about 36%. A smaller λ means that a given data sample is "forgotten" more quickly. For example, if λ is equal to 0.9800 then T$_0$=50 samples, meaning that the 50$^{th}$ sample receives a weight of about 36%. However, if λ=0.9999 then T$_0$=10,000, meaning that sample number 10,000 receives a weight of 36%. In the upper limit, if λ=1 then T$_0$=∞, meaning that a data sample is never "forgotten" (it always receives a weight of 100%).

The sampling rate (how many times a second the acceleration is measured) affects the how λ changes the system identifier. If samples are taken 1000 times per second then data may be "forgotten" rapidly on the time scale of CPR compressions. For example, if the sample rate is 1000 times per second and T$_0$=1000 then data from just 1 second in the past is given a weight of 36%. In practice, the sampling rate may vary from about 100 samples per second to about 2000 samples per second. A useful sample rate for signal processing acceleration measurements during CPR is about 500 samples per second. In other embodiments the sample rate may be faster, but every certain number of samples may be ignored. For example, samples may be taken at 1000 samples per second, but every other sample ignored. This process, known as decimation, has the same effect as a slower sample rate.

In the preceding discussion the forgetting factor was a fixed number; it did not change with time. However, λ can vary with time so that the system identifier may adapt to changing situations. For example, λ may vary during a ventilation pause and in one embodiment λ increases during a ventilation pause. The effect of increasing λ during ventilation pauses is to discard data points very quickly. Thus, the compression monitor will not report a change in compression depth during a ventilation pause.

In addition to adding a forgetting factor to the system identification function, the choice of updating step affects the quality of the model. (Although only some of the system identification techniques require an update; for example, a Kalman filter requires an updating step). The update step can be implemented using a variety of methods. Some system identifiers may be solved analytically, such as the Kalman filter, and the updating step may be solved analytically. Other system identifiers must be solved numerically. Three updating methods that may be used when a numerical solution is required are a Gauss-Newton update, a gradient update, and a Levenberg-Marquardt update. The Gauss-Newton update converges to an accurate fit of the actual solution, though it requires a large number of steps (and thus more computation time). The gradient update converges quickly but does not converge as accurately to the actual solution as the Gauss-Newton update. The methods may be combined. The gradient update is used first to converge the fit quickly and then the identifier switches to the Gauss-Newton update to achieve the final fit. This combined technique is known as a Levenberg-Marquardt update.

Mathematically the Gauss-Newton update may be expressed as:

$R(t)=R(t-1)+\gamma(t)[\phi(t)\phi^T(t)-R(t-1)]$.

Mathematically the gradient update may be expressed as:

$R(t)=I|\phi(t)|^2=R(t-a)+\gamma(t)[I|\phi(t)|^2-R(t-1)]$.

In both equations R(t) is the Hessian of the identification criterion, R(t−1) is the Hessian of the identification criterion in the previous time step, γ(t) is the updating gain (which is related to the forgetting factor), and φ(t) is the regression vector.

The choice of updating gain is another step that is used in many recursive system identification functions. The choice of updating gain may be expressed mathematically as:

$\gamma(t)=(1+\lambda(t)/\gamma(t-1))^{-1}$.

Thus, the updating gain is related to the forgetting factor.

With regard to model order selection, the recursive system identification techniques fit a system model to input-output data. The structure of that model must be determined before the recursive. The standard way of solving the model structure problem is to solve a wide range of model structures and then select which model fits the data best. A simple measure of model fit, like the mean squared error, tends to over-estimate the model order and fit to the process or measurement noise. If a model is under-estimated, critical components of the system might be missed. Several measures of model fit, or metrics, are evaluated over a range of model orders. The model order is the number of terms used in the model. The smallest model order that minimizes the fit is the appropriate model.

Several techniques can be used to estimate smallest model order, including final prediction error (FPE), Akaike's information criterion (AIC), maximum description length (a variant of the AIC), and statistical hypothesis testing (such as the student's t-test). The final prediction error can be expressed mathematically as:

$$FPE = \frac{V(1+d/N)}{(1-d/N)}, \quad (11)$$

where V is the quadratic loss function, d is the size of the model order, and N is the number of data points.

Akaike's information criterion may be expressed as:

$$AIC = \log[V(1+2(d/N))], \quad (12)$$

where V is the quadratic loss function. The quadratic loss function may be any quadratic function that relates the additional cost function of using additional terms.

Figure 30:
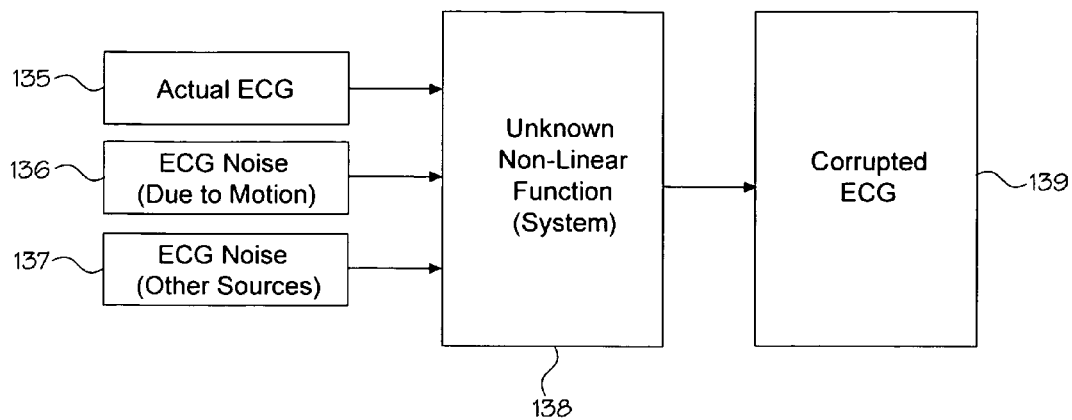
FIG. 30 is a block diagram of how an actual ECG signal is converted into a corrupted ECG signal.

The system identification techniques described above have been described in the context of solving the problem of estimating actual compression depth from a raw acceleration measurement. These techniques may also be used to process a noisy ECG signal. FIG. 30 is a block diagram illustrating the problem of ECG noise caused by CPR and other sources of noise. Stated differently, FIG. 30 is a block diagram of how a theoretical actual ECG signal 135 and the noise sources are combined to produce the measured ECG (which contains the motion corrupting artifact). The ECG noise, comprising ECG noise due to compressions 136 and other sources of noise 137, are combined with the actual ECG by an unknown linear or non-linear function known as the system 138. The primary source of noise in the ECG is due to the motion of compressions, though other sources of noise exist and may be accounted for by the solution presented below. The system produces a corrupted ECG 139 which, if left unprocessed, cannot be used to accurately report the electrical activity of the patient's heart. In addition, the system combines the ECG noise and the actual ECG in a way that causes the ECG noise to overlap the actual ECG in the frequency domain. Thus, a simple bandpass filter is insufficient to accurately process the corrupted ECG. (A simple bandpass filter will eliminate important components of the actual ECG as well as eliminating the ECG noise).

Figure 31:
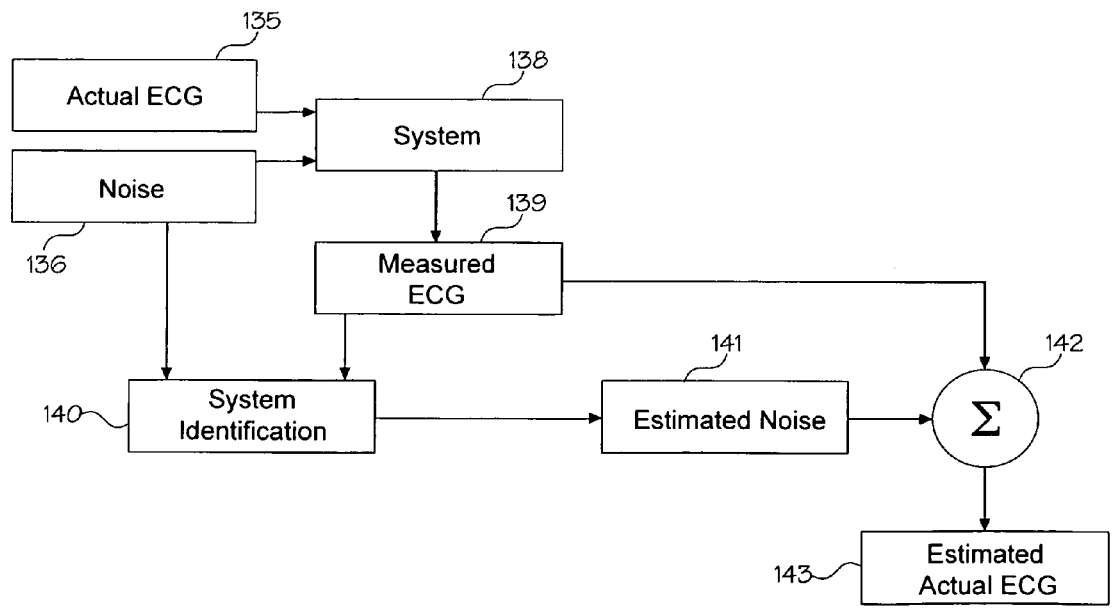
FIG. 31 is a block diagram of a general solution for converting a motion corrupted ECG signal into an estimated actual ECG signal.

FIG. 31 is a block diagram of a general solution to the problem illustrated in FIG. 30 and illustrates the process of converting a motion corrupted ECG signal into an estimated actual ECG signal. As with FIG. 30, the system 138 combines the actual ECG 135 and the ECG noise 136 to produce the corrupted ECG 139 that is measured by an observer. Next, the measured ECG 139 and a reference corresponding to the ECG noise 136 are provided to a system identifier 140. For example, since CPR induced motion is the largest cause of ECG noise, a signal corresponding to CPR induced motion may be provided to the system identifier. Specifically, a force transducer may be disposed on a compression monitor (or on the patient or rescuer) such that the force transducer measures force during a compression. A signal corresponding to the force is provided to the system identifier as a reference signal. Other signals corresponding to CPR induced motion may comprise various parameters of an automatic CPR device. For example, a signal correlating to the displacement of a drive shaft or other component can be correlated to the CPR motion, a signal corresponding to the change in current or voltage required to drive the device can be correlated to the CPR motion, or signals produced by optical or rotary encoders may be correlated to the CPR motion.

The system identifier models the system and then estimates the noise component of the measured ECG signal (the estimated noise 141). The estimated ECG noise 141 and the measured ECG 139 are then provided to a means for combining signals 142, which combines the ECG noise and the measured ECG to produce the estimated actual ECG 143. Since the estimated actual ECG is produced during compressions, the signal processing method allows the ECG sensor to detect the heart's normal sinus rhythm even during compressions. Thus, there is no need to periodically pause compressions to check for the existence of a pulse. As a result, the overall quality of CPR increases and the patient is more likely to survive.

The system identifier 140 may comprise similar kinds of functions and methods as described in the context of the signal processing methods of FIG. 29. For example, the recursive least squares method described in the context of FIG. 29 may be used to identify the noise component of the measured ECG signal.

Figure 32:
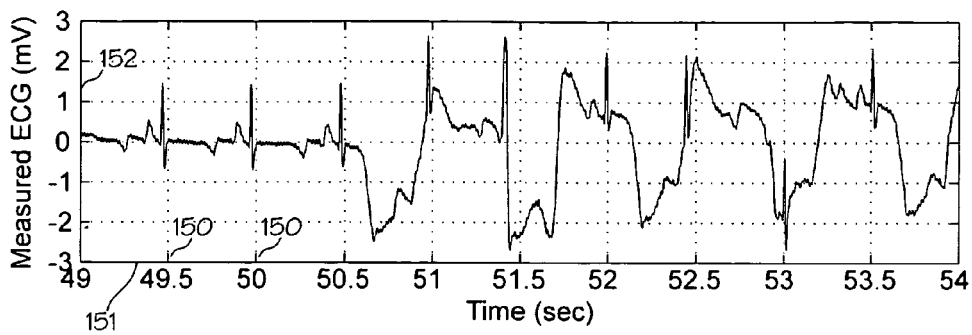
FIG. 32 is a graph of a pig's ECG signal that is corrupted by noise caused by chest compressions.
Figure 33:
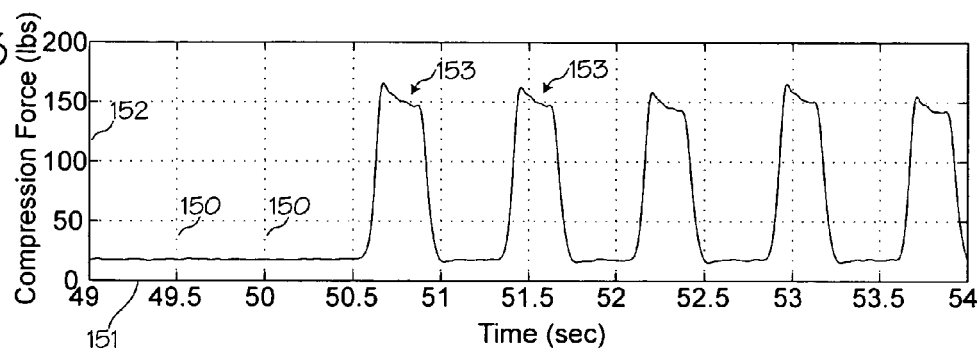
FIG. 33 is a graph of CPR motion where CPR is performed on a pig.
Figure 34:
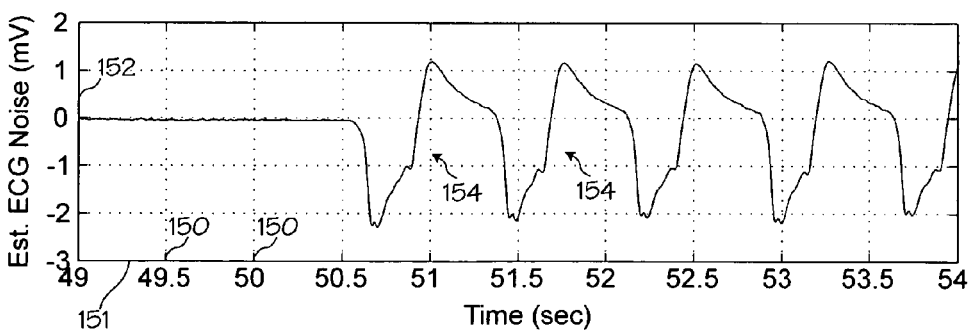
FIG. 34 is a graph of the pig's estimated ECG noise signal.
Figure 35:
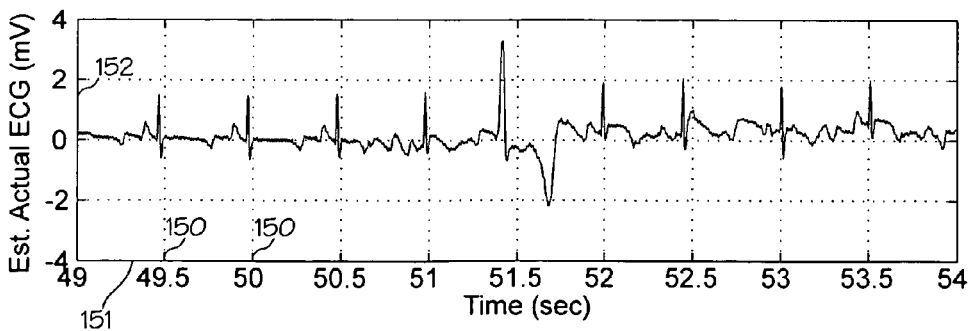
FIG. 35 is a graph of the pig's estimated actual ECG signal.

FIGS. 32 through 35 show the effect of using the method of FIG. 31 to estimate a pig's actual ECG when the ECG is measured during chest compressions. For all four graphs each time marker 150 along time scale 151 corresponds to the same time marker in the other three graphs, thus making possible a direct comparison of one graph to each of the other graphs. However, the voltage scales 152 of FIGS. 32, 34, and 35 are slightly different from each other.

FIG. 32 is a graph (millivolts versus milliseconds) of an actual pig's ECG signal that is corrupted by noise caused by chest compressions. FIG. 32 represents the ECG measured during compressions without signal processing.

FIG. 33 is a graph of force versus time for an actual CPR motion signal. The motion signal comprises a time varying force signal and corresponds to the force a CPR device places on the pig's chest while performing chest compressions. The force peaks 153 correspond to the maximum depth of compressions. In the case of a compression monitor, the motion signal could comprise a time varying force signal that corresponds to the force placed on the patient's chest while a rescuer or automatic CPR device performs chest compressions. In this case a force transducer disposed on a compression monitor (such as on the back of the compression monitor) measures the force of compressions and produces the force signal. The force signal is later correlated to the ECG noise. The force transducer or other force sensor may also be disposed under the patient's back and then operably connected to the compression monitor.

FIG. 34 is a graph of voltage versus time for the estimated ECG noise signal caused by the chest compressions shown in FIG. 33. A comparison of FIGS. 33 and 34 shows that the time varying pressure signal corresponds directly to incidence of ECG noise. In other words, the pressure peaks 153 caused by chest compressions correspond to the incidence of noise peaks 154.

The system identifier 140 used to generate the estimated noise component of the noisy ECG comprises a recursive least squares method as described in the context of FIG. 29. The autoregressive order was selected to be equal to 1. The moving average order was selected to be 10. The autoregressive order was selected to be 10. The derivative order was also selected to be 0. (The derivative order is a linear or non-linear term used in the system model; specifically it may be either a truncated positive derivative or a truncated negative derivative. The non-linear terms are extensions of the recursive least squares model fit algorithm). The forgetting factor, λ, was selected to be 1.0000.

FIG. 35 is a graph of the pig's estimated actual ECG signal. The graph of FIG. 35 is generated by subtracting the estimated noise signal of FIG. 34 from the measured ECG signal of FIG. 32. The estimated actual ECG signal corresponds closely to the pig's actual ECG signal.

The signal processing methods described in the context of noisy ECG signals (FIGS. 30 and 31) and noisy acceleration signals (FIGS. 28 and 29), as well as the techniques described in relation to the baseline limiter and the peak limiter, may also be used to estimate the actual value of the patient's transthoracic impedance (the chest's electrical resistance or impedance). The estimated actual value of the patient's transthoracic impedance may be used to determine the amount of voltage needed to shock the patient with a defibrillator.

As compressions are applied to the patient the measured value of the transthoracic impedance becomes noisy. The general signal processing solutions and the limiters already described may be used to identify, isolate, and eliminate the noise component of the measured transthoracic impedance. Thus, the actual value of the transthoracic impedance may be estimated.

The estimated actual value of the transthoracic impedance may be provided to a means for defibrillating the patient. The means for defibrillating the patient uses the estimated actual value of the transthoracic impedance to determine the exact voltage necessary to apply an effective shock to the patient. Since the exact value of the voltage required is also known, the defibrillator can be used efficiently (thus preserving battery life and making the device safer).

Since both the estimated actual ECG and the estimated actual transthoracic impedance are known, an automated CPR device equipped with an AED (automated external defibrillator) may perform defibrillation shocks to a patient without stopping compressions. The device may determine when defibrillation is appropriate based on the estimated actual ECG and may apply the appropriate defibrillation voltage based on the estimated actual transthoracic impedance. Since compressions do not stop during defibrillation, the patient's blood flow does not stop (meaning the patient is more likely to survive).

The compression monitor using these signal processing techniques (for either chest depth measurement or ECG measurement) may be used with any means for compressing the chest of the patient. A means for compressing the chest may comprise manual CPR, electro-stimulation, a means for performing automatic CPR (including belts, straps, pistons, and plates that are driven by motors or manual levers), or other devices suitable for compressing the chest. Examples of automatic CPR devices may be found in our own patent Sherman et al., Modular CPR Assist Device, U.S. Pat. No. 6,066,106 (May 23, 2000) and in our application CPR Assist Device with Pressure Bladder Feedback, U.S. application Ser. No. 09/866,377 filed May 25, 2001. (Both devices use optical or rotary encoders disposed on a compression belt or a drive shaft or spool to measure the amount of belt pay out or compression depth). The accelerometer itself may be disposed in any location where the accelerometer experiences the downward or upward acceleration of compressions. For example, the accelerometer may be disposed within or otherwise disposed on the means for compressing the chest, such as a compression belt. (In the case of manual compressions, the compression monitor may be disposed beneath a rescuer's hands while the rescuer performs compressions, or the compression monitor may be otherwise disposed on the rescuer's hands, wrist, or arms.)

If the compression monitor is provided with a means for sensing the tilt of the accelerometer, such as a three-axis accelerometer, three-axis load sensor, three-axis displacement measurement device, or the tilt sensor shown in our own U.S. Pat. No. 6,390,996 to Halperin et al., then the user feedback system can prompt the rescuer with respect to compression efficiency. For most patients, compressions are most efficient when compressions are performed perpendicular to the sternum (straight down in most cases). The tilt sensor measures the angle at which compressions are performed and the compression monitor prompts the rescuer to adjust the angle if the angle falls outside a particular range.

The compression monitor and signal processor may also be operably connected to a defibrillator. While the rescuer or device is performing compressions the defibrillator or compression monitor tracks the patient's ECG. If the compression monitor's processor measures an ECG signal that indicates that the patient would benefit from a shock, then the rescuer would be instructed to apply a defibrillation shock or to allow an AED to administer a shock. A means for estimating the patient's actual ECG during compressions comprises our own method disclosed in U.S. Pat. No. 6,390,996 to Halperin et al and the method disclosed in this application.

The compression monitor may also be operably connected to a means for performing ventilation. After the rescuer has performed an appropriate number of compressions, such as 15, the compression monitor will instruct the rescuer to pause compressions. The means for performing ventilation will then administer an appropriate number of ventilations. After ventilations the compression monitor may evaluate the patient's condition. If the patient still requires compressions, then the compression monitor will instruct the rescuer to resume compressions. The means for performing ventilation may comprise the rescuer, a bag or balloon, a positive pressure ventilator, an electro-ventilator such as those shown in our own patent Sherman et al., *Chest Compression Device with Electro-Stimulation*, U.S. Pat. No. 6,213,960 (Apr. 10, 2001), or other means for performing ventilation.

The compression monitor may also be provided with a means for communication that allows the compression monitor to communicate with a remote network. The means for communication comprises a signal carrier and a compression monitor communicator. The signal carrier may comprise a telephone line, direct connection cables, a dedicated digital network, a cell phone network, a satellite communication array, radio or other electromagnetic waves, a LED, the internet, or other means for carrying a signal. The compression monitor communicator may comprise a radio or other electromagnetic wave transmitter and receiver, a LED, a modem, or other means for transmitting and receiving a signal carrier. The means for communication allows the compression monitor to upload or download information from a remote network. The compression monitor may also be provided with a global positioning satellite reader (GPS reader), speakers, keypads, telephones, modems, microphones, cameras, or visual displays to allow the user to receive and input information. Data may be exchanged by the means for communication using known communication standards, such as the bluetooth standard.

The remote network may provide other information to the compression monitor and may also receive information from the compression monitor. For example, the compression monitor may be updated with additional waveforms, patient treatment history, ventilation ratios, or other compression-related information of use in a subsequent or current emergency. In the case when a group of monitors are assigned to a single network, each compression monitor may be tracked separately by the remote network and provided with different information (if warranted). The remote network itself may comprise one or more computers, the internet, another CPR-related device, or a human operator capable of remotely programming the compression monitor or remotely prompting the rescuer.

In use, the compression monitor is provided at a location, such as a shopping mall or a public place, and is stored until needed. Upon activation, the compression monitor establishes communication between it and the remote network, which may be a computer located in a call center. Emergency responders, such as police, fire, and ambulance services, may be notified of the activation and directed to go to a location pinpointed by the GPS reader or to contact the person activating the compression monitor. The remote network computer and an operator trained to use the computer may provide voice assistance to the rescuer while monitoring real time streaming data from the compression monitor. The operator or computer may from time to time provide other information to the compression monitor or rescuer. For example, the compression monitor may be provided with data corresponding to what waveform the rescuer should be prompted to perform and the operator may verbally coach the rescuer. In turn, the compression monitor provides data, such as compression depth, rate, force, waveform, and duty cycle, to the operator and computer for medical analysis. Should the rescuer become fatigued then the operator can provide a substitute waveform that is easier for the rescuer to follow. Likewise, the operator can provide verbal encouragement to the rescuer.

Another use for the means for communication is to enable automatic or prompted maintenance of the compression monitor. Either periodically or continuously the compression monitor communicates with a remote network and transmits data such as battery life and status, number of uses, whether any parts need to be replaced, and other information concerning maintenance status. In response, the compression monitor either automatically performs maintenance on itself, such as a software upgrade, or it prompts a user to perform maintenance upon it. Another use for the means for communication is to enable the compression monitor to communicate with additional products used during an emergency response. Example of such a products include those products described above, a drug dispenser, or any other product useful for responding to the emergency.

An example of combined product use begins with a rescuer beginning manual resuscitation with the compression monitor. Emergency medical personnel arrive and deploy an automated chest compression device equipped with an AED. The automated chest compression device is adapted to exchange information with the compression monitor. After the automated chest compression device is deployed, the compression monitor automatically communicates with the chest compression device and transfers relevant treatment history to it, such as time under compression, quality of compressions as compared to an ideal waveform, ECG history, and other relevant medical data. Based on the information provided by the compression monitor, the automated chest compression device may provide a defibrillation shock to the patient before beginning compressions. Conversely, the automated chest compression device may determine, based on the transferred data, that chest compressions must be continued before administering a shock.

Another example of a combined product is a compression monitor and a separate signal processor. The signal processor may be provided as one or more physical chips (hardware) or may be provided as a computer program (software). In either case, the signal processor may be a separate unit or module and need not be built directly into the monitor. Accordingly, the signal processing units may be provided as stand-alone products. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A device for measuring depth of chest compressions, said device comprising:
    an accelerometer capable of producing an acceleration signal corresponding to the acceleration of chest compressions;
    a means for integrating the acceleration signal, said means for integrating operably connected to the accelerometer, and said means for integrating capable of producing a measured depth signal corresponding to the measured depth of chest compressions; and
    a processor operably connected to the means for integrating, said processor programmed to produce an estimated actual depth signal corresponding to the estimated actual depth of chest compressions by calculating an autoregressive moving average of the measured depth signal.

2. The device of claim 1 further comprising a display operably connected to the processor, and wherein the display is capable of displaying the estimated actual depth signal.

3. The device of claim 1 further comprising a means for user feedback operably connected to the processor, wherein the means for user feedback is capable of providing feedback that indicates whether chest compressions fall within a predetermined range of values.

4. The device of claim 1 further comprising:
    a means for measuring an ECG signal of a patient, said ECG signal having a noise component and an actual component;
    a means for estimating the noise component of the ECG signal operably connected to the means for measuring the ECG signal and to the processor;
    wherein the processor is further programmed to produce the estimated actual depth signal when the noise component of the ECG signal falls within a predetermined range.

5. The device of claim 4 further comprising a display operably connected to the processor, and wherein the display is capable of displaying the estimated actual depth signal.

6. The device of claim 4 further comprising a means for user feedback operably connected to the processor, wherein the means for user feedback is capable of providing feedback that indicates whether chest compressions fall within a predetermined range of values.

7. The device of claim 6 wherein the processor is further capable of measuring the rate of chest compressions and wherein the means for user feedback is further capable of displaying the rate of chest compressions.

8. The device of claim 6 wherein the processor is further capable of measuring the duty cycle of chest compressions and wherein the means for user feedback is further capable of displaying the duty cycle of chest compressions.

9. The device of claim 1 further comprising a means for performing ventilation capable of ventilating the patient during CPR.

10. The device of claim 9 wherein the means for ventilation comprises a means for performing electro-ventilation.

11. A device for performing chest compressions, said device comprising:
 a means for performing chest compressions on a patient;
 an accelerometer capable of producing an acceleration signal corresponding to the acceleration of chest compressions;
 a means for integrating the acceleration signal, said means for integrating operably connected to the accelerometer, and said means for integrating capable of producing a measured depth signal corresponding to the measured depth of chest compressions;
 a processor operably connected to the means for integrating and to the means for performing chest compressions, said processor capable of producing an estimated actual depth signal corresponding to the estimated actual depth of chest compressions by calculating an autoregressive moving average of the measured depth signal;
 wherein the means for performing chest compressions is capable of adjusting the depth of chest compressions based on the estimated actual depth signal.

12. The device of claim 11 wherein the means for performing chest compressions comprises an automatic chest compression device.

13. The device of claim 11 further comprising:
 a means for measuring an ECG signal of a patient, said ECG signal having a noise component and an actual component;
 a means for estimating the noise component of the ECG signal operably connected to the means for measuring the ECG signal and to the processor;
 wherein the processor is further programmed to produce the estimated actual depth signal when the noise component of the ECG signal falls within a predetermined range.

14. The device of claim 13 wherein the means for performing chest compressions comprises an automatic chest compression device.

15. The device of claim 11 further comprising a means for performing ventilation capable of ventilating the patient during CPR.

16. The device of claim 15 wherein the means for ventilation comprises a means for performing electro-ventilation.

17. The device of claim 11 further comprising a display operably connected to the processor, and wherein the display is capable of displaying the estimated actual depth signal.

18. The device of claim 11 further comprising a means for user feedback operably connected to the processor, wherein the means for user feedback is capable of providing feedback that indicates whether chest compressions fall within a predetermined range of values.

19. The device of claim 18 wherein the processor is further capable of measuring the rate of chest compressions and wherein the means for user feedback is further capable of displaying the rate of chest compressions.

20. The device of claim 18 wherein the processor is further capable of measuring the duty cycle of chest compressions and wherein the means for user feedback is further capable of displaying the duty cycle of chest compressions.

21. A device for measuring depth of chest compressions, said device comprising:
 an accelerometer capable of producing an acceleration signal corresponding to the acceleration of chest compressions, said acceleration signal having a noise component and an actual component;
 a processor operably connected to the accelerometer, said processor capable of producing, from the acceleration signal, an estimated actual acceleration signal corresponding to the estimated actual acceleration of chest compressions;
 wherein the processor further comprises:
  a system identifier operably connected to the accelerometer, said system identifier capable of producing an estimated noise signal corresponding to the noise component of the acceleration signal;
  wherein the system identifier produces the estimated noise signal by processing the measured acceleration and at least one error source reference;
  a means for combining signals operably connected to the system identifier and to the accelerometer, said means for combining signals capable of combining the acceleration signal and the estimated noise signal to produce the estimated actual acceleration signal; and
 a means for integrating the estimated actual acceleration signal, said means for integrating operably connected to the processor, and said means for integrating capable of integrating the estimated actual acceleration signal to produce an estimated actual depth signal corresponding to the estimated actual depth of chest compressions.

22. The device of claim 21 further comprising a display operably connected to the processor, and wherein the display is capable of displaying the estimated actual depth signal.

23. The device of claim 21 further comprising a means for user feedback operably connected to the processor, wherein the means for user feedback is capable of providing feedback that indicates whether chest compressions fall within a predetermined range of values.

24. The device of claim 23 wherein the processor is further capable of measuring the rate of chest compressions and wherein the means for user feedback is further capable of displaying the rate of chest compressions.

25. The device of claim 23 wherein the processor is further capable of measuring the duty cycle of chest compressions and wherein the means for user feedback is further capable of displaying the duty cycle of chest compressions.

26. The device of claim 21 further comprising:
 a means for measuring an ECG signal of a patient, said ECG signal having a noise component and an actual component;
 a means for estimating the noise component of the ECG signal operably connected to the means for measuring the ECG signal and to the processor;
 wherein the processor is further programmed to produce the estimated actual depth signal when the noise component of the ECG signal falls within a predetermined range.

27. The device of claim 26 further comprising a display operably connected to the processor, and wherein the display is capable of displaying the estimated actual depth signal.

28. The device of claim 26 further comprising a means for user feedback operably connected to the processor, wherein the means for user feedback is capable of providing feedback that indicates whether chest compressions fall within a predetermined range of values.

29. The device of claim 28 wherein the processor is further capable of measuring the rate of chest compressions and wherein the means for user feedback is further capable of displaying the rate of chest compressions.

30. The device of claim 28 wherein the processor is further capable of measuring the duty cycle of chest compressions and wherein the means for user feedback is further capable of displaying the duty cycle of chest compressions.

31. The device of claim 21 further comprising a means for performing ventilation capable of ventilating the patient during CPR.

32. The device of claim 31 wherein the means for ventilation comprises a means for performing electro-ventilation.

33. A device for performing chest compressions, said device comprising:
   a means for performing chest compressions on a patient;
   an accelerometer capable of producing an acceleration signal corresponding to the acceleration of chest compressions, said acceleration signal having a noise component and an actual component;
   a processor operably connected to the accelerometer, said processor capable of producing, from the acceleration signal, an estimated actual acceleration signal corresponding to the estimated actual acceleration of chest compressions;
   wherein the processor further comprises:
      a system identifier operably connected to the accelerometer, said system identifier capable of producing an estimated noise signal corresponding to the noise component of the acceleration signal;
      wherein the system identifier produces the estimated noise signal by processing the measured acceleration and at least one error source reference;
      a means for combining signals operably connected to the system identifier and to the accelerometer, said means for combining signals capable of combining the acceleration signal and the estimated noise signal to produce the estimated actual acceleration signal; and
   a means for integrating the estimated actual acceleration signal, said means for integrating operably connected to the processor, and said means for integrating capable of integrating the estimated actual acceleration signal to produce an estimated actual depth signal corresponding to the estimated actual depth of chest compressions;
   wherein the means for performing chest compressions is capable of adjusting the depth of chest compressions based on the estimated actual depth signal.

34. The device of claim 33 further comprising a display operably connected to the processor, and wherein the display is capable of displaying the estimated actual depth signal.

35. The device of claim 33 further comprising a means for user feedback operably connected to the processor, wherein the means for user feedback is capable of providing feedback that indicates whether chest compressions fall within a predetermined range of values.

36. The device of claim 35 wherein the processor is further capable of measuring the rate of chest compressions and wherein the means for user feedback is further capable of displaying the rate of chest compressions.

37. The device of claim 35 wherein the processor is further capable of measuring the duty cycle of chest compressions and wherein the means for user feedback is further capable of displaying the duty cycle of chest compressions.

38. The device of claim 33 further comprising:
   a means for measuring an ECG signal of a patient, said ECG signal having a noise component and an actual component;
   a means for estimating the noise component of the ECG signal operably connected to the means for measuring the ECG signal and to the processor;
   wherein the processor is further programmed to produce the estimated actual depth signal when the noise component of the ECG signal falls within a predetermined range.

39. The device of claim 38 further comprising a display operably connected to the processor, and wherein the display is capable of displaying the estimated actual depth signal.

40. The device of claim 38 further comprising a means for user feedback operably connected to the processor, wherein the means for user feedback is capable of providing feedback that indicates whether chest compressions fall within a predetermined range of values.

41. The device of claim 40 wherein the processor is further capable of measuring the rate of chest compressions and wherein the means for user feedback is further capable of displaying the rate of chest compressions.

42. The device of claim 40 wherein the processor is further capable of measuring the duty cycle of chest compressions and wherein the means for user feedback is further capable of displaying the duty cycle of chest compressions.

43. The device of claim 33 further comprising a means for performing ventilation capable of ventilating the patient during CPR.

44. The device of claim 33 wherein the means for ventilation comprises a means for performing electro-ventilation.

* * * * *